US012575904B2

(12) United States Patent
Sun et al.

(10) Patent No.: US 12,575,904 B2
(45) Date of Patent: Mar. 17, 2026

(54) ENDOSCOPE CONTROL METHOD AND SURGICAL ROBOT SYSTEM

(71) Applicant: Peking Union Med. College Hosp., Chinese Acad. of Med. Sci. and Peking Union Med. College, Beijing (CN)

(72) Inventors: Dawei Sun, Beijing (CN); Lan Zhu, Beijing (CN); Chang Ren, Beijing (CN)

(73) Assignee: PEKING UNION MEDICAL COLLEGE HOSPITAL, CHINESE ACADEMY OF MEDICAL SCIENCES AND PEKING UNION MEDICAL COLLEGE, Beijing (CN)

( * ) Notice: Subject to any disclaimer, the term of this patent is extended or adjusted under 35 U.S.C. 154(b) by 706 days.

(21) Appl. No.: 18/050,865

(22) Filed: Oct. 28, 2022

(65) Prior Publication Data

US 2024/0115339 A1     Apr. 11, 2024

(30) Foreign Application Priority Data

Oct. 11, 2022     (CN) .......................... 202211241616.9

(51) Int. Cl.
*A61B 34/37*          (2016.01)
*A61B 1/00*           (2006.01)
(Continued)

(52) U.S. Cl.
CPC .......... *A61B 34/37* (2016.02); *A61B 1/00009* (2013.01); *A61B 1/00052* (2013.01);
(Continued)

(58) Field of Classification Search
CPC ......... A61B 34/37; A61B 34/30; A61B 34/20; A61B 34/10; A61B 34/35; A61B 1/00009;
(Continued)

(56) References Cited

U.S. PATENT DOCUMENTS

2006/0030841 A1*  2/2006  Madhani ................ A61B 34/77
                                                            606/1
2013/0038689 A1*  2/2013  McDowall ............. H04N 23/10
                                                            348/45
(Continued)

FOREIGN PATENT DOCUMENTS

CN          104814712 A        8/2015
CN          106456267 A        2/2017
CN          113453606 A        9/2021

OTHER PUBLICATIONS

Search Report issued for Chinese Patent Application No. 202211241616.9, dated Sep. 15, 2025, 5 pages including English machine translation.

*Primary Examiner* — Anh Tuan T Nguyen
*Assistant Examiner* — Li-Ting Song
(74) *Attorney, Agent, or Firm* — HSML P.C.

(57)                    ABSTRACT

The present disclosure relates to the field of medical instruments, disclosing an endoscope control method. The method comprises: controlling a motion of an endoscope, the endoscope comprising a main body, a first imaging unit, a second imaging unit and an end instrument protruding from a distal end of the main body; obtaining a first image from the first imaging unit; obtaining a second image from the second imaging unit, wherein the first and the second images have different fields of view and include images of the end instrument; based on the first and second images, generating a composite scene image to remove an actual image of the
(Continued)

1300 determine a supplementary image based on the first image or the second image, wherein the supplementary image includes a portion of the second image or the first image that is blocked by the end instrument — 1301 determine a first environment image or a second environment image based on the first image or the second image, wherein the first environment image and the second environment image do not include the image of the end instrument — 1303 stitch the first environment image or the second environment image and the supplementary image to generate a stitched image — 1305

1900

1970
control device 1990
display device 1920
1930
1940

1950
1960
1980 end instrument; and generating a virtual image of the end instrument in the composite scene image.

17 Claims, 13 Drawing Sheets

(51) Int. Cl.
*A61B 34/30* (2016.01)
*A61B 90/00* (2016.01)

(52) U.S. Cl.
CPC .... *A61B 1/00149* (2013.01); *A61B 2034/301* (2016.02); *A61B 2090/365* (2016.02)

(58) Field of Classification Search
CPC ............ A61B 1/00052; A61B 1/00149; A61B 1/0005; A61B 1/00193; A61B 1/00194; A61B 1/05; A61B 1/000095; A61B 2034/301; A61B 2090/365; G06T 2207/10068; G06T 2207/10012–10021
See application file for complete search history.

(56) References Cited

U.S. PATENT DOCUMENTS

| | | | |
|---|---|---|---|
| 2013/0096377 A1* | 4/2013 | Duindam ............... | A61B 10/02 |
| | | | 600/104 |
| 2015/0170381 A1* | 6/2015 | Liu ........................... | G06T 7/74 |
| | | | 348/77 |
| 2018/0228555 A1* | 8/2018 | Charron ............... | A61B 90/361 |
| 2019/0008367 A1 | 1/2019 | Ishikawa et al. | |
| 2020/0078103 A1* | 3/2020 | Duindam ............... | A61B 1/009 |
| 2020/0253673 A1* | 8/2020 | Azizian ................. | A61B 34/35 |
| 2021/0128243 A1* | 5/2021 | Kumar ................... | A61B 90/36 |
| 2021/0267695 A1* | 9/2021 | Hazelton ............... | A61B 1/012 |
| 2022/0094901 A1* | 3/2022 | Nonn ..................... | H04N 13/25 |
| 2023/0180998 A1* | 6/2023 | Mizutani ............. | A61B 1/0004 |
| | | | 600/101 |
| 2024/0285366 A1* | 8/2024 | Frimer ................ | A61B 1/0005 |

* cited by examiner

600

7212    7211    721

900

<u>1000</u>

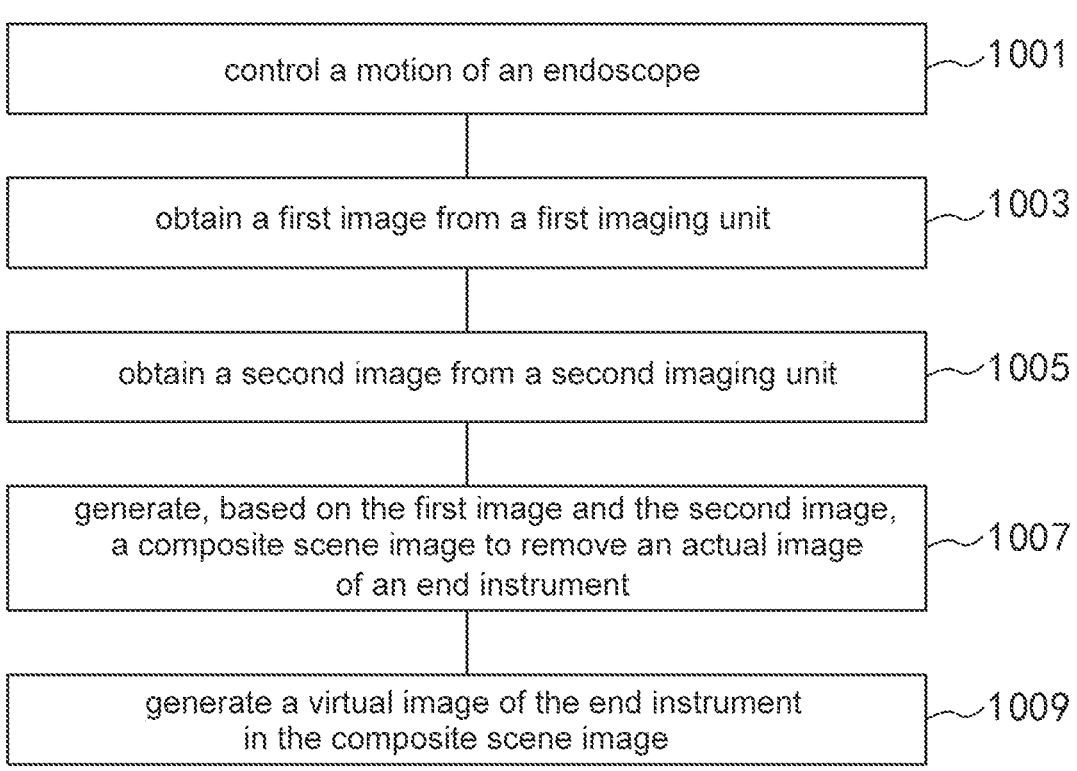

| control a motion of an endoscope | ~1001 |

| obtain a first image from a first imaging unit | ~1003 |

| obtain a second image from a second imaging unit | ~1005 |

| generate, based on the first image and the second image, a composite scene image to remove an actual image of an end instrument | ~1007 |

| generate a virtual image of the end instrument in the composite scene image | ~1009 |

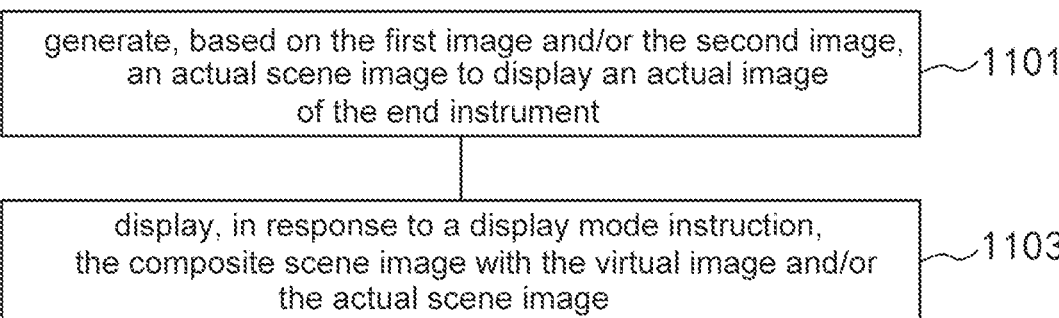

| generate, based on the first image and/or the second image, an actual scene image to display an actual image of the end instrument | ~1101 |

| display, in response to a display mode instruction, the composite scene image with the virtual image and/or the actual scene image | ~1103 |

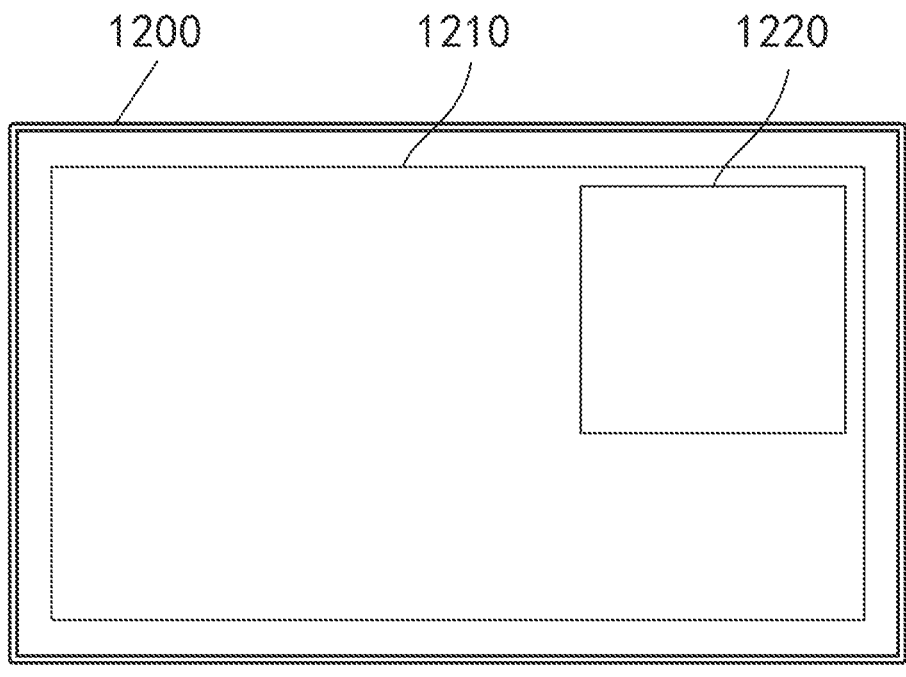

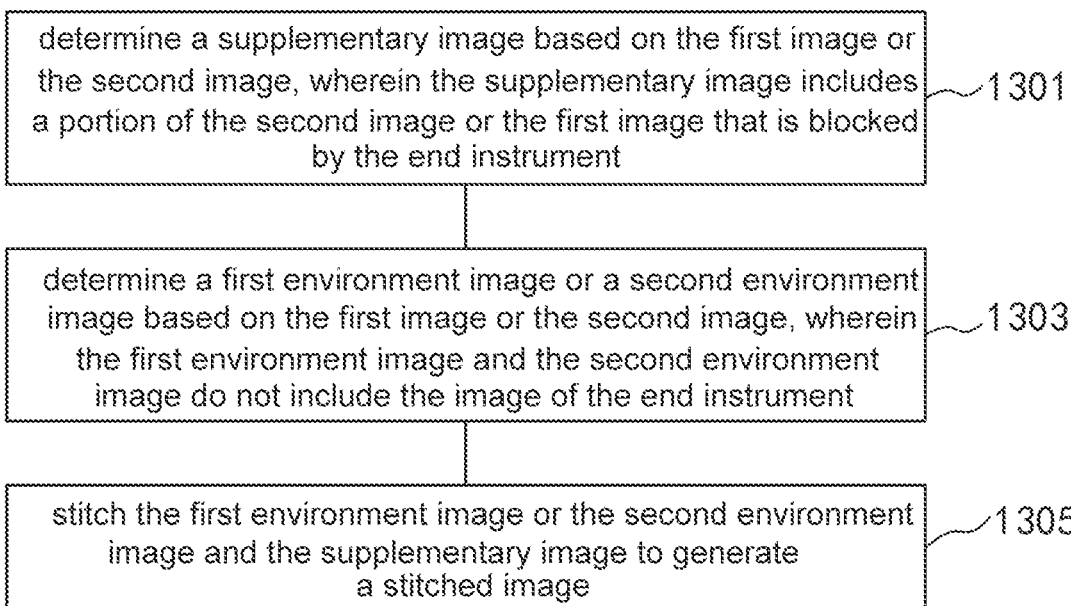

| | |
|---|---|
| determine a supplementary image based on the first image or the second image, wherein the supplementary image includes a portion of the second image or the first image that is blocked by the end instrument | 1301 |
| determine a first environment image or a second environment image based on the first image or the second image, wherein the first environment image and the second environment image do not include the image of the end instrument | 1303 |
| stitch the first environment image or the second environment image and the supplementary image to generate a stitched image | 1305 |

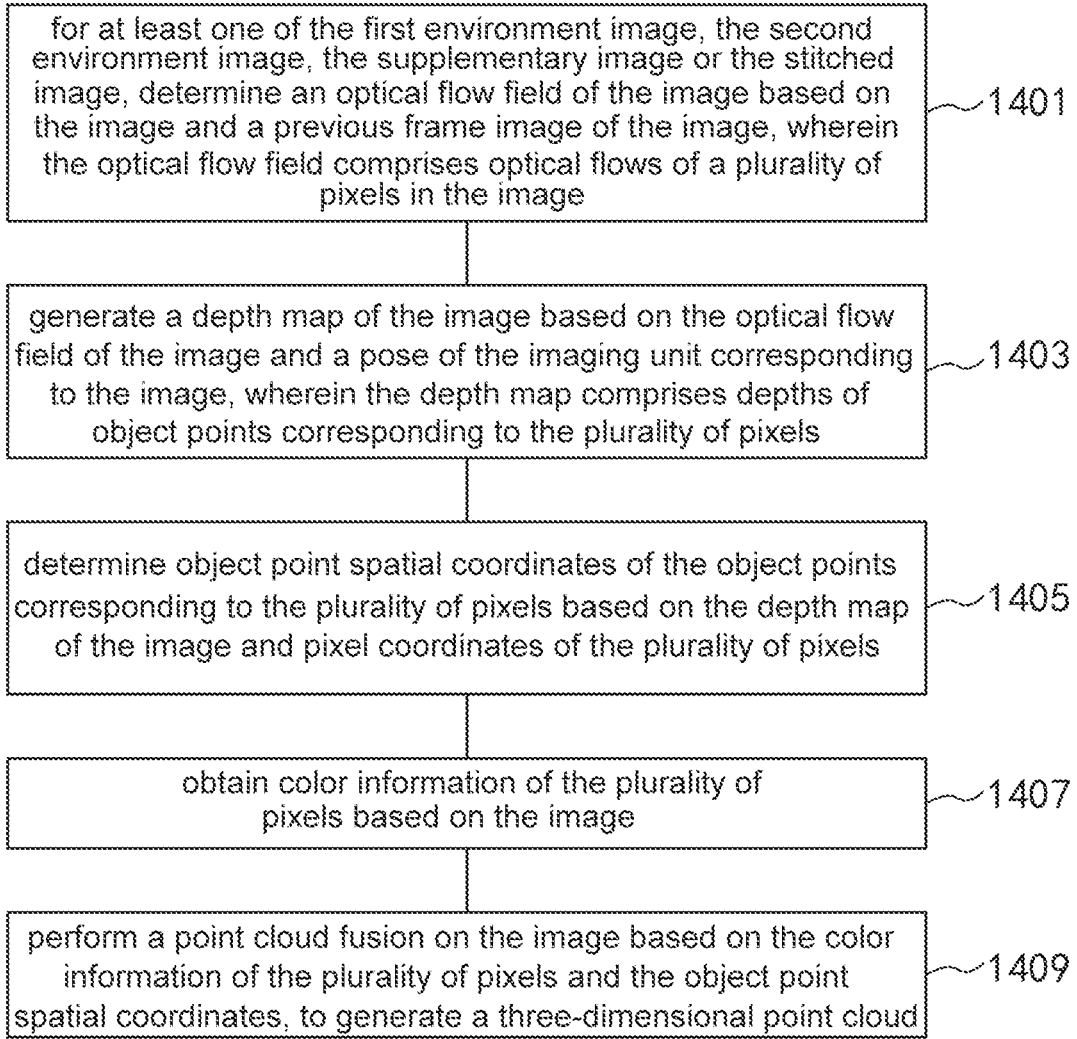

for at least one of the first environment image, the second environment image, the supplementary image or the stitched image, determine an optical flow field of the image based on the image and a previous frame image of the image, wherein the optical flow field comprises optical flows of a plurality of pixels in the image — 1401 generate a depth map of the image based on the optical flow field of the image and a pose of the imaging unit corresponding to the image, wherein the depth map comprises depths of object points corresponding to the plurality of pixels — 1403 determine object point spatial coordinates of the object points corresponding to the plurality of pixels based on the depth map of the image and pixel coordinates of the plurality of pixels — 1405 obtain color information of the plurality of pixels based on the image — 1407 perform a point cloud fusion on the image based on the color information of the plurality of pixels and the object point spatial coordinates, to generate a three-dimensional point cloud — 1409

FIG. 14

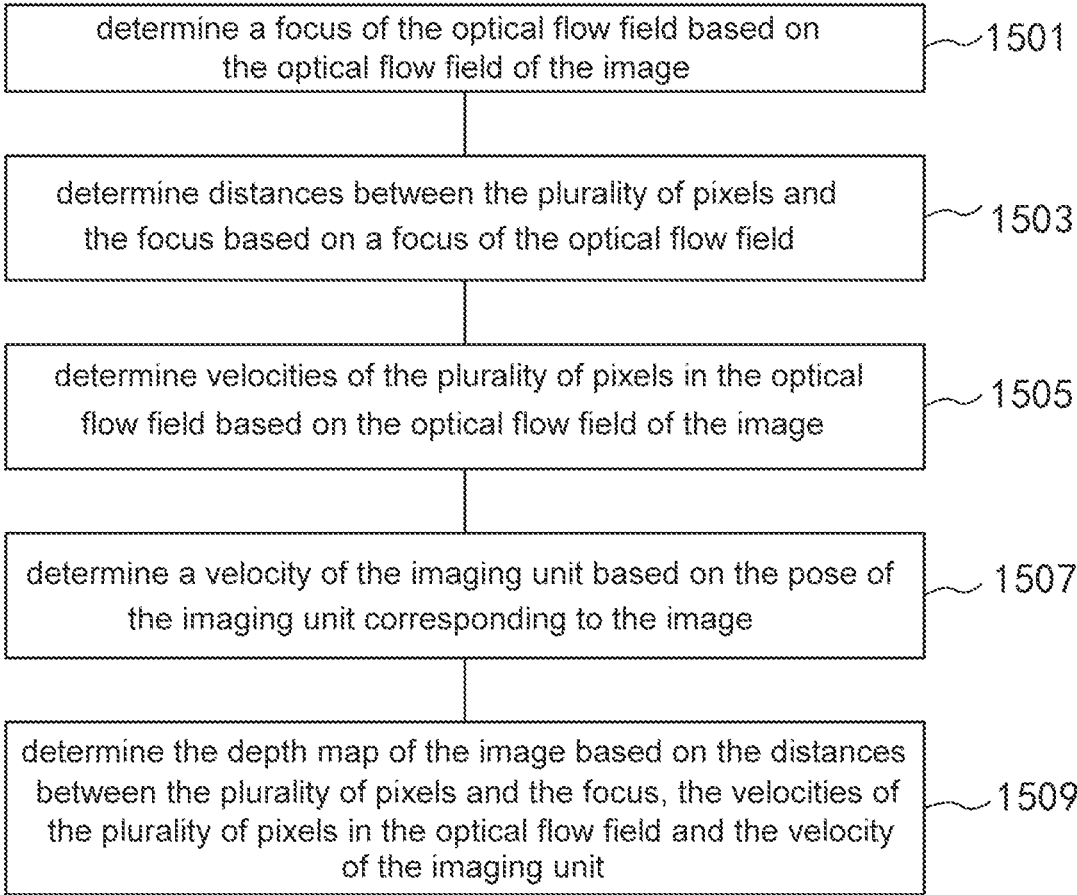

1500 determine a focus of the optical flow field based on the optical flow field of the image — 1501 determine distances between the plurality of pixels and the focus based on a focus of the optical flow field — 1503 determine velocities of the plurality of pixels in the optical flow field based on the optical flow field of the image — 1505 determine a velocity of the imaging unit based on the pose of the imaging unit corresponding to the image — 1507 determine the depth map of the image based on the distances between the plurality of pixels and the focus, the velocities of the plurality of pixels in the optical flow field and the velocity of the imaging unit — 1509

FIG. 15

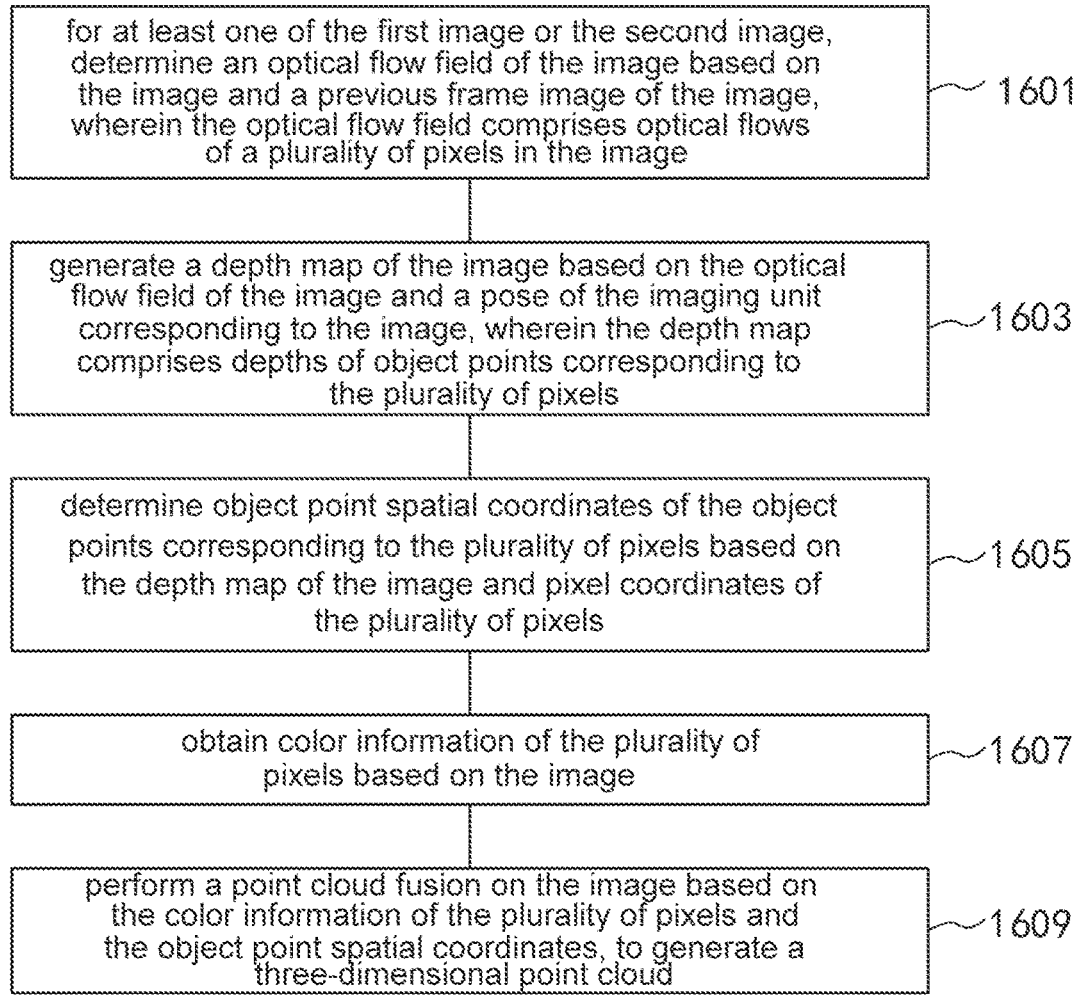

1600 for at least one of the first image or the second image, determine an optical flow field of the image based on the image and a previous frame image of the image, wherein the optical flow field comprises optical flows of a plurality of pixels in the image — 1601 generate a depth map of the image based on the optical flow field of the image and a pose of the imaging unit corresponding to the image, wherein the depth map comprises depths of object points corresponding to the plurality of pixels — 1603 determine object point spatial coordinates of the object points corresponding to the plurality of pixels based on the depth map of the image and pixel coordinates of the plurality of pixels — 1605 obtain color information of the plurality of pixels based on the image — 1607 perform a point cloud fusion on the image based on the color information of the plurality of pixels and the object point spatial coordinates, to generate a three-dimensional point cloud — 1609

FIG. 16

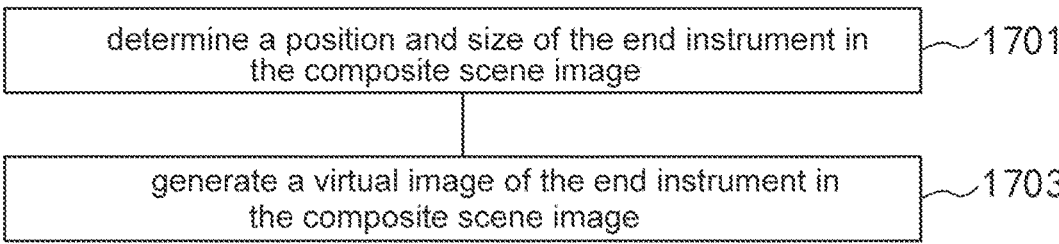

1700 determine a position and size of the end instrument in the composite scene image — 1701 generate a virtual image of the end instrument in the composite scene image — 1703

FIG. 17

ENDOSCOPE CONTROL METHOD AND SURGICAL ROBOT SYSTEM

TECHNICAL FIELD

The present disclosure relates to the field of medical instruments, and in particular to an endoscope control method and surgical robot system.

BACKGROUND

In modern endoscope minimally invasive surgery, an endoscope is required to reach inside the cavity to take images. Sometimes, an end instrument is also integrated on some endoscopes to juggle image acquisitions and surgical operations. However, the end instrument protruding from a distal end can limit a visual field of the endoscope, thereby affecting the accuracy of a surgeon's surgical operation diagnosis.

SUMMARY OF THE INVENTION

In some embodiments, the present disclosure provides an endoscope control method. The method may comprise: controlling a motion of an endoscope, the endoscope comprising a main body, a first imaging unit, a second imaging unit and an end instrument protruding from a distal end of the main body; obtaining a first image from the first imaging unit; obtaining a second image from the second imaging unit, wherein the first and the second images have different fields of view and include images of the end instrument; generating, based on the first and second images, a composite scene image to remove the actual image of the end instrument; and generating a virtual image of the end instrument in the composite scene image.

In some embodiments, the present disclosure provides a robot system comprising: a motion arm; an endoscope disposed at an end of the motion arm, the endoscope including: an operating arm including at least one segment capable of being bent controllably; a main body disposed at a distal end of the operating arm; a first imaging unit for taking a first image; a second imaging unit for taking a second image; and an end instrument configured to protrude from a distal end of the main body; a control device configured to perform the methods of any of some embodiments of the present disclosure; and a display device for displaying images based on instructions output by the control device.

In some embodiments, the present disclosure provides a computer device comprising: a memory for storing at least one instruction; and a processor coupled to the memory and for executing at least one instruction to perform the method of any of some embodiments of the present disclosure.

In some embodiments, the present disclosure provides a computer-readable storage medium for storing at least one instruction that when executed by a computer, causes the computer to perform the method of any of some embodiments of the present disclosure.

BRIEF DESCRIPTION OF THE DRAWINGS

In order to explain the technical solutions in the embodiments of the present disclosure more clearly, the accompanying drawings used in the description of the embodiments of the present disclosure will be briefly introduced below. Obviously, the accompanying drawings in the following description only show some of the embodiments of the present disclosure, and for those of ordinary skill in the art, other embodiments would also have been obtained from the contents of the embodiments of the present disclosure and these accompanying drawings without involving any inventive effort.

FIG. 6A and FIG. 6B show a structure diagram of the end instrument according to other embodiments of the present disclosure, wherein FIG. 6A is a front view of the end instrument, FIG. 6B is a rear view of the end instrument;

FIG. 10 shows a flowchart of an endoscope control method according to some embodiments of the present disclosure;

FIG. 11 shows a flowchart of a method of displaying a scene image based on a display mode instruction according to some embodiments of the present disclosure;

FIG. 12 shows a schematic diagram of a multi-scene display on a display device according to some embodiments of the present disclosure;

FIG. 13 shows a flowchart of a method of generating a composite scene image based on a first image and a second image according to some embodiments of the present disclosure;

FIG. 14 shows a flowchart of a method of generating a three-dimensional composite scene image based on a first image and a second image according to some embodiments of the present disclosure;

FIG. 15 shows a flowchart of a method of generating a depth map based on an optical flow field and a pose of the imaging unit according to some embodiments of the present disclosure;

FIG. 16 shows a flowchart of a method of generating a three-dimensional actual scene image based on a first image and/or a second image according to some embodiments of the present disclosure;

FIG. 17 shows a flowchart of a method of generating a virtual image of the end instrument in the composite scene image according to some embodiments of the present disclosure;

DETAILED DESCRIPTION

Figure 1:
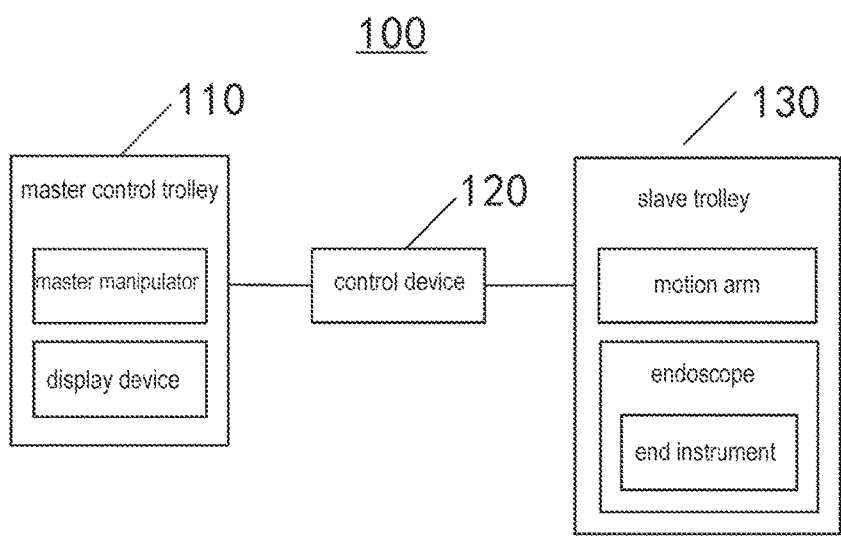
FIG. 1 shows a structure block diagram of a robot system according to some embodiments of the present disclosure.

To make the solved technical problems, used technical solutions, and achieved technical effects of the present disclosure more clearly, the technical solutions of the embodiments of the present disclosure will be further described in detail below with reference to the accompanying drawings. Obviously, the described embodiments are only exemplary embodiments, but not all of embodiments, of the present disclosure.

In the description of the present disclosure, it should be noted that, orientational or positional relationships indicated by the terms "center", "upper", "lower", "left", "right", "vertical", "horizontal", "inner", "outer" and the like are the orientational or positional relationships shown based on the accompanying drawings, and are only for ease of describing the present disclosure and simplifying the description, rather than indicating or implying that the apparatus or element referred to must have a specific orientation or be constructed and operated in a specific orientation, and therefore cannot be construed as limiting the present disclosure. In addition, the terms "first" and "second" are used for descriptive purposes only, and cannot be understood as indicating or implying relative importance. In the description of the present disclosure, it should be noted that, unless otherwise specified and defined, the term "mount", "connected", and "connect", or "couple" should be comprehended in a broad sense. For example, the term may be a fixed connection or a detachable connection; or may be a mechanical connection or an electrical connection; may be a direct connection or an indirect connection via an intermediate medium; or may be internal communication between two elements. For those of ordinary skill in the art, specific meanings of the foregoing terms in the present disclosure may be understood based on specific situations.

In the present disclosure, an end close to an operator (e.g., a surgeon) is defined as a proximal end, a proximal portion, a rear end, or a rear portion, and an end close to a patient who requires surgery is defined as a distal end, a distal portion, a front end, or a front portion. It may be understood by those skilled in the art that the embodiments of the present disclosure may be used for a medical instrument or a surgical robot, and may also be used for other non-medical apparatus.

In the present disclosure, a reference coordinate system may be understood as a coordinate system capable of describing a pose of an object. According to actual positioning requirements, the reference coordinate system may be chosen to take an origin of a virtual reference object or an origin of a real reference object as an origin of the coordinate system. In some embodiments, the reference coordinate system may be a world coordinate system, or a coordinate system of the space where a certain point on a master manipulator, a motion arm, an end of an operating arm, a main body of an endoscope, an end instrument, a first imaging unit, a second imaging unit or a lumen is located, or the operator's own perception coordinate system and the like.

In the present disclosure, the object may be understood as a subject or a target needed to be positioned, such as the operating arm or the end of the operating arm, and may also be a certain point on the lumen. The pose of the operating arm or a portion (e.g., the end) thereof may refer to a pose of a coordinate system defined by the operating arm, a portion of the operating arm or a portion rigidly extending on the operating arm (e.g., the main body of the endoscope or the end instrument) relative to the reference coordinate system.

FIG. 1 shows a structure block diagram of a robot system 100 according to some embodiments of the present disclosure. In some embodiments, as shown in FIG. 1, the robot system 100 may include a master control trolley 110, a slave trolley 130 and a control device 120. The control device 120 may be communicatively connected with the master control trolley 110 and the slave trolley 130, for example, via cable connections, or via wireless connections, to achieve the communication with the master control trolley 110 and the slave trolley 130. The master control trolley 110, which functions as an operating terminal and an interacting terminal of the robot system 100, may include a master manipulator for an operator to operate remotely, and a display device for images. The slave trolley 130, which functions as a working terminal of the robot system 100, includes a motion arm for performing tasks, and an endoscope disposed at an end of the motion arm. With the control device 120 to achieve the master-slave mapping between the master manipulator in the master control trolley 110 and the endoscope in the slave trolley 130, the motion control of the endoscope by the master manipulator is achieved. In some embodiments, a distal portion of the endoscope is provided to be able to enter into an operating area via a lumen through a tube sleeve, a sheath sleeve, etc., photograph a target area in the scene and generate a two-dimensional or three-dimensional scene image to be displayed on the display device. The endoscope may include an end instrument disposed at its distal end, and the end instrument may be a surgical tool, for example, a clamp-type device, a hemostatic device, a drug delivery device, etc. In some embodiments, the robot system 100 may be configured to be capable of processing the captured scene image to generate multiple images such as a composite scene image comprising an actual scene image of the end instrument and/or comprising a virtual image of the end instrument, and selectively display these images on the display device based on operating instructions. By controlling the robot system 100, it is possible to operate the end instrument to, at the surgical site, perform surgical tasks on an object (e.g., pathological tissue, etc.) to be operated in a contact or non-contact way in the case of obtaining the field of view of the operating area and a surgical site. The tube sleeve and the sheath sleeve may be fixed to human or animal body etc., forming an opening (for example an incision or a natural opening), the lumen may be the trachea, esophagus, vagina, intestine, etc., the operating area may be the area where the surgical tasks are performed, and the scene may be the lumen or the operating area. Those skilled in the art will appreciate that the master control trolley 110 and the slave trolley 130 may employ other structures or forms, such as a base or a bracket and the like. The master control trolley 110 and the slave trolley 130 may also be integrated on the same device.

Figure 2:
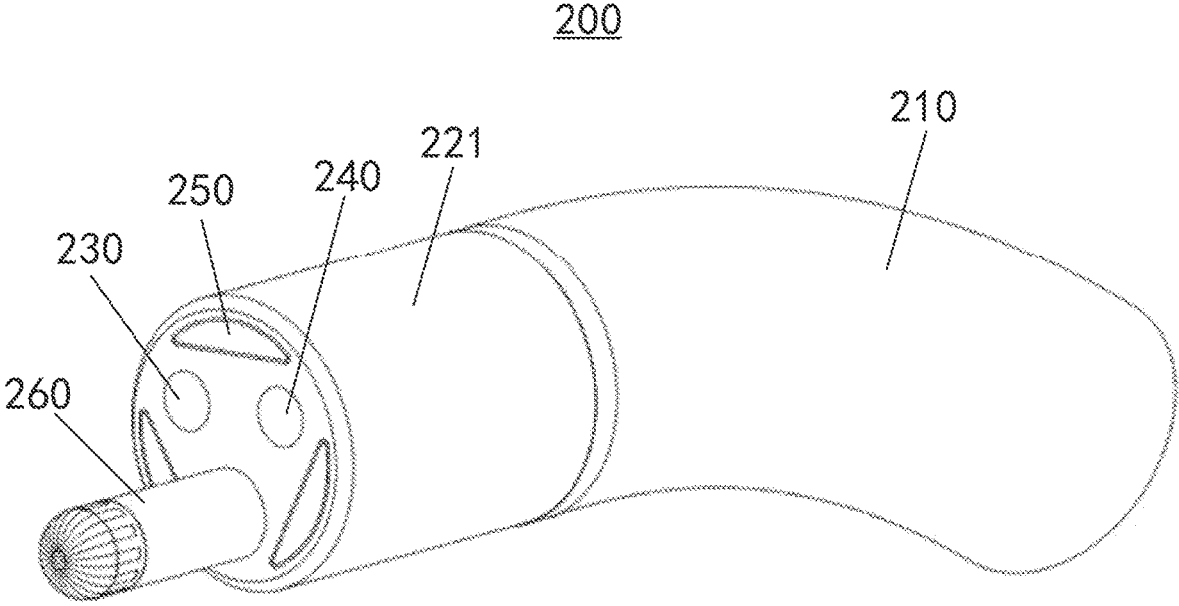
FIG. 2 shows a structure diagram of an endoscope according to some embodiments of the present disclosure.
Figure 3:
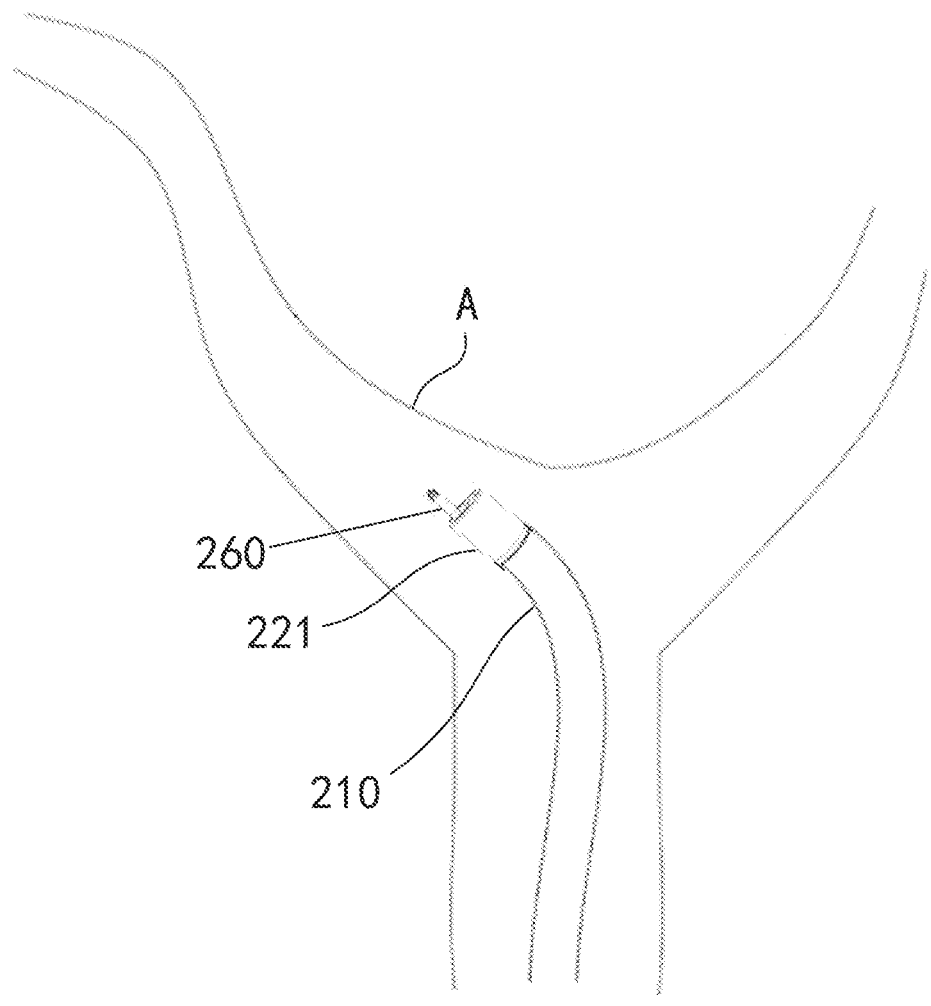
FIG. 3 shows a structure diagram of the endoscope located within an internal lumen according to some embodiments of the present disclosure.

FIG. 2 shows a structure diagram of an endoscope 200 according to some embodiments of the present disclosure. FIG. 3 shows a structure diagram of the endoscope 200 being located within a lumen A in a body (for example in a human body or an animal body) according to some embodiments of the present disclosure. As shown in FIGS. 2 and 3, the endoscope 200 may include an operating arm 210 and an endoscope main body 221. In some embodiments, the operating arm 210 may be a continuum body capable of being bent controllably, may include a segment (e.g., a segment 800 shown in FIG. 8) bendable on at least one degree of freedom at the distal end, and the distal end of the operating arm 210 is provided with the endoscope main body 221. The operating arm 210 may be disposed at a distal end of a motion arm of the slave trolley 130, and the pose of the master manipulator and the pose of the end of the operating arm have a master-slave motion mapping relationship. In some embodiments, the operating arm may change the steering of the endoscope main body 221 based on operating instructions issued by the operator to avoid vital organs within the body or to adapt to the complex curved lumen A, so that the endoscope main body 221 feeds into the operating area through the lumen A or withdraw from the lumen A. In some embodiments, the operating arm may adjust the pose of the endoscope main body 221 based on the operating instructions, so as to facilitate an imaging unit (e.g., a first imaging unit 230, a second imaging unit 240 shown in FIG. 2 and FIG. 3, or a first imaging unit 430, a second imaging unit 440 shown in FIG. 4) on the endoscope main body 221 to photograph the operating area, and to enable an end instrument (e.g., an end instrument 260 shown in FIG. 2 and FIG. 3, an end instrument 460 shown in FIG. 4, an end instrument 500 shown in FIG. 5 or an end instrument 600 shown in FIG. 6A and FIG. 6B) on the endoscope main body 221 to align with the surgical site in the operating area.

The endoscope 200 may further include the first imaging unit 230, the second imaging unit 240, and the end instrument 260. In some embodiments, the endoscope 200 may further include at least one illumination unit 250. As shown in FIG. 2, the endoscope main body 221 is in a roughly columnar shape, and its cross-sectional shape may be circular or oval to meet different functional needs.

The first imaging unit 230 may be used to take a first image, and the second imaging unit 240 may be used to take a second image. In some embodiments, the first imaging unit 230 and the second imaging unit 240 may be, for example, a CCD camera, and comprise a set of image sensors and image lenses, respectively, and the image lens may be disposed at a distal end of the image sensor and align with at least corresponding image sensor, so as to facilitate the image sensor to photograph a target area in the scene through the image lens. In some embodiments, the image lens may include a plurality of convex lenses and concave lenses, and the plurality of convex lenses and concave lenses form an optical imaging system by a distribution arrangement. For example, the distal surface of the image lens may be a curved convex lens, for example, a spherical lens, an ellipsoidal lens, a cone lens, a frustum lens, and the like. The image lens may include at least one convex surface to increase a range of the field of view that can be photographed.

The illumination unit 250 is used to provide illumination, so as to facilitate the photographing of the first imaging unit 230 and the second imaging unit 240. As shown in FIG. 2, in some embodiments, three illumination units 250 are provided along a perimeter edge of the endoscope 200, located between two imaging units or between an imaging unit and the end instrument 260, respectively, but not limited thereto. The number and arrangement mode of illumination units 250 may be changed according to actual needs. For example, the number of illumination units 250 may also be two, located on the left and right sides of the endoscope 200. Alternatively, in order to further increase the illumination intensity, the number of illumination units 250 may also be greater than three. In some embodiments, the cross-section of the illumination unit 250 may be crescent-shaped, thereby making full use of the space on the endoscope 200, facilitating to achieve miniaturization of the endoscope and increase the field of view of illumination. However, the shape of the cross-section of the illumination unit 250 is not limited thereto, and the illumination unit 250 may also be in other shapes. In some embodiments, the illumination unit 250 may include a light source and one or more fibers coupled to the light source. In the interior of the endoscope main body 221, an illumination channel may be formed for disposing the fiber. In some embodiments, the light source of the illumination unit 250 may be, for example, an LED light source.

In some embodiments, the end instrument 260 may be configured to protrude from the distal end of the endoscope main body 221 to perform surgical tasks, as described below in detail. In some embodiments, the endoscope 200 may further include a ranging unit (not shown in the figure) for measuring the distance between the endoscope 200 and the surgical site. The ranging unit may be a ranging sensor, for example, a laser ranging sensor and the like. By disposing the ranging unit, the distance between the endoscope 200 (e.g., the distal surface of the endoscope main body 221) and the operating site can be determined, thereby the distance between the end instrument 260 and the operating site can be further determined.

Figure 4:
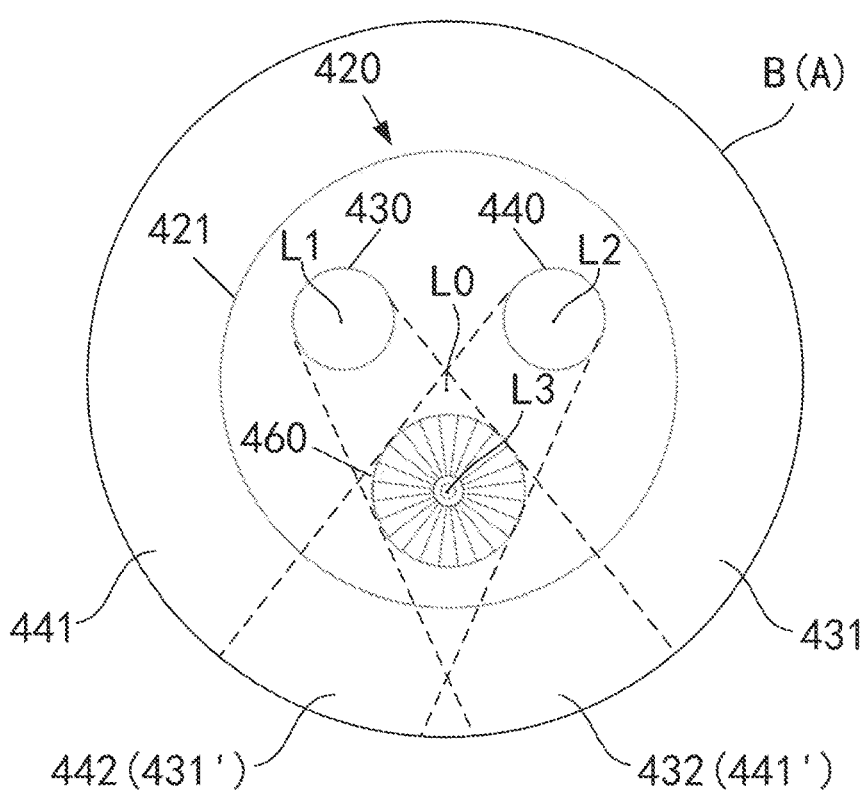
FIG. 4 shows a schematic diagram of relative positional relationships between a first imaging unit, a second imaging unit and an end instrument according to some embodiments of the present disclosure.

FIG. 4 shows a schematic diagram of relative positional relationships between a first imaging unit 430, a second imaging unit 440 and an end instrument 460 according to some embodiments of the present disclosure. As shown in FIG. 4, in some embodiments, the first imaging unit 430 may be configured to be located on one side of the endoscope main body 421 with respect to the end instrument 460, and has a first field of view corresponding to the orientation of its own optical axis L1.

It should be understood that the first field of view of the first imaging unit 430 is formed as a roughly conical shape centered on the optical axis L1. FIG. 4 schematically shows a cross-section of the first field of view, a plane where the cross-section is located is perpendicular to the optical axis L1. Further, it should be understood that a plane where the first imaging unit 430 and the second imaging unit 440 as described below is located, the distal surface of the end instrument 460, the cross-sections of the first field of view and the second field of view as described below are not located in the same plane, but for ease of description, FIG. 4 shows, on the same plane, the plane where the first imaging unit 430 and the second imaging unit 440 as described below is located, the distal surface of the end instrument 460, the cross-sections of the first field of view and the second field of view as described below.

The first field of view includes a field of view 431 and a field of view 432, wherein the field of view 431 is a portion of the first field of view that is not blocked by the end instrument 460, and the field of view 432 is a portion of the first field of view that is blocked by the end instrument 460. As shown in FIG. 4, the range of the field of view 431 and the field of view 432 covers the cross-section of the entire operating area B (or the lumen A). The first imaging unit 430 may take a first image of the operating area B (or the lumen A) in the first field of view, and the first image includes an image of the end instrument 460.

The second imaging unit 440 may be configured to be located on the other side (opposite side) of the endoscope main body 421 with respect to the end instrument 460, and has a second field of view corresponding to the orientation of its own optical axis L2. Similar to the first imaging unit 430, the second field of view of the second imaging unit 440 is formed as a roughly conical shape centered on the optical axis L2. FIG. 4 schematically shows a cross-section of the second field of view, a plane where the cross-section is located is perpendicular to the optical axis L2. The second field of view includes a field of view 441 and a field of view 442, wherein the field of view 441 is a portion of the second field of view that is not blocked by the end instrument 460, and the field of view 442 is a portion of the second field of view that is blocked by the end instrument 460. As shown in FIG. 4, the range of the field of view 441 and the field of view 442 covers the cross-section of the entire operating area B (or the lumen A). The second imaging unit 440 may take a second image of the operating area B (or the lumen A) in the second field of view, and the second image has a different field of view from that of the first image and includes an image of the end instrument 460.

In some embodiments, the optical axis L1 of the first imaging unit 430 and the optical axis L2 of the second imaging unit 440 may be parallel to an axis L0 of the endoscope main body 421, respectively, and an axis L3 of the end instrument 460 may be parallel to the axis L0 of the endoscope main body 421 and deviate from a connecting line between the first imaging unit 430 and the second imaging unit 440. For example, the first imaging unit 430, the second imaging unit 440 and the end instrument 460 may be configured such that the optical axis L1 of the first imaging unit 430, the optical axis L2 of the second imaging unit 440 and the axis L3 of the end instrument 460 are perpendicular to the distal surface of the endoscope main body 421, respectively, the first imaging unit 430 and the second imaging unit 440 are symmetrically arranged with respect to the end instrument 460, and the axis L3 of the end instrument 460 is located below the connecting line between the first imaging unit 430 and the second imaging unit 440. By configuring the optical axes of the first imaging unit 430 and the second imaging unit 440 to be parallel to each other, and arranging the first imaging unit 430 and the second imaging unit 440 symmetrically on both sides of the end instrument 460, it can be achieved that the first image captured by the first imaging unit 430 and the second image captured by the second imaging unit 440 are symmetrical with each other, thereby facilitating the processing of the first image and the second image, improving a picture generation quality and a picture processing speed of the robot system.

Those skilled in the art will appreciate that, although in the present disclosure, for ease of description, the first image and the second image are described as examples, the embodiments of the present disclosure may be applied to the processing of a sequence of first images and a sequence of second images, to form continuous video frame processing and displaying. Thus, the capturing, processing and displaying of the sequence of first images and the sequence of second images fall within the scope of the present disclosure and fall within the scope of protection of the claims of the present disclosure.

In the present disclosure, the end instrument (e.g., the end instrument 260 shown in FIG. 2 and FIG. 3, the end instrument 460 shown in FIG. 4, the end instrument 500 shown in FIG. 5 or the end instrument 600 shown in FIG. 6A and FIG. 6B) may include a surgical tool, such as a hemostatic device (e.g., an electrocoagulation hemostatic device), a clamp-type device, a drug delivery device and the like, to adapt to different surgical needs. The following describes the end instrument as the electrocoagulation hemostatic device.

In some embodiments, the end instrument may be configured such that its proximal end is fixedly connected to the distal end of the endoscope main body, whereby the pose of the end instrument can be changed by adjusting the pose of the endoscope main body, enabling the end instrument to be aligned to the surgical site in the operating area. In some embodiments, the end instrument may be a bipolar electrocoagulation hemostatic device. For example, the end instrument may include at least one first electrode, at least one second electrode and an insulating body, wherein the at least one first electrode and the at least one second electrode are alternately arranged on a circumferential outward side of the insulating body, at least a portion of the first electrode is exposed, and at least a portion of the second electrode is exposed. When a high-frequency current is turned on, at least the exposed portion of the first electrode and at least the exposed portion of the second electrode form a circuit for electrocoagulation hemostasis.

Figure 5:
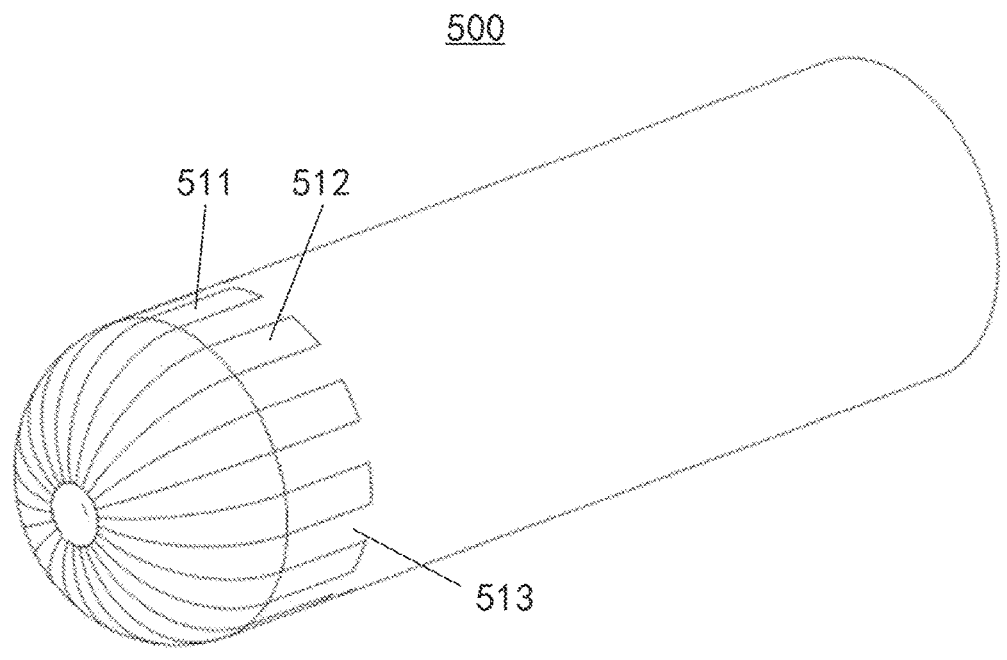
FIG. 5 shows a structure diagram of the end instrument according to some embodiments of the present disclosure.

FIG. 5 shows a structure diagram of the end instrument 500 according to some embodiments of the present disclosure. As shown in FIG. 5, in some embodiments, the end instrument 500 is formed into a roughly round-headed cylindrical shape. It should be understood that the end instrument 500 includes, but is not limited to, the above shape, and may also be formed as a hemispherical shape, a round-stage shape and the like. The end instrument 500 includes at least one first electrode 511, at least one second electrode 512 and an insulating body 513. The insulating body 513 may be made of an insulating material such as plastic, ceramic, or mica. In some embodiments, the at least one first electrode 511 and the at least one second electrode 512 may be alternately arranged on a circumferential outward side of the insulating body 513. For example, the first electrode 511 and the second electrode 512 may be arranged alternately at a predetermined interval on the circumferential outward side of the insulating body 513. Though in some embodiments, the first electrode 511 and the second electrode 512 may extend from a distal end to a proximal end on the circumference of the insulating body 513 along a generatrix of the cylinder, the first electrode 511 and the second electrode 512 are not limited thereto, and they may also be formed into a roughly helical shape, alternately coiled around the circumferential outward side of the insulating body 513.

In some embodiments, the end instrument 500 may be mounted on the main body of the endoscope, or may also be molded into one piece with the main body of the endoscope. For example, a rear end of the insulating body 513 may be formed with a mounting structure (e.g., shown in FIG. 7) for mounting the end instrument 500 on the main body of the endoscope. For example, the insulating body 513 may be formed with a recess at the proximal end as the mounting structure, and an internal thread may be formed on the circumferential inner wall of the recess, thereby connecting with the main body of the endoscope by the thread. It should be understood that the mounting structure of the insulating body 513 is not limited to the above structure. For example, the mounting structure of the insulating body 513 may also be formed as a boss having an external thread, or may be a structure that may be connected to the main body of the endoscope by a snap-in connection.

Figure 6A:
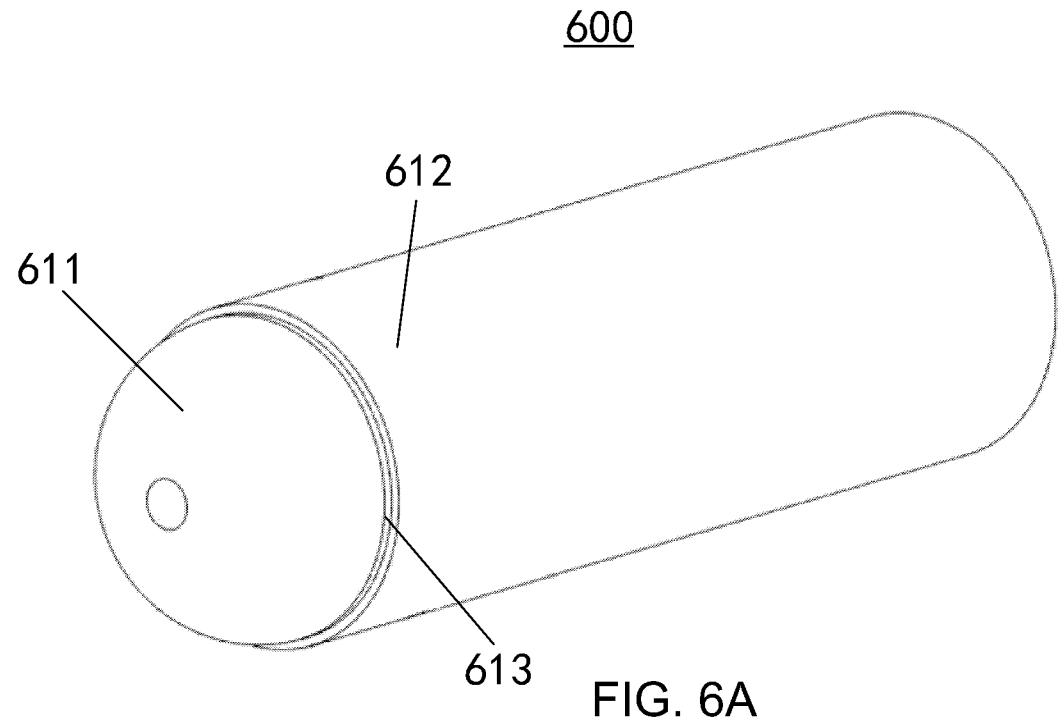
Figure 6B:
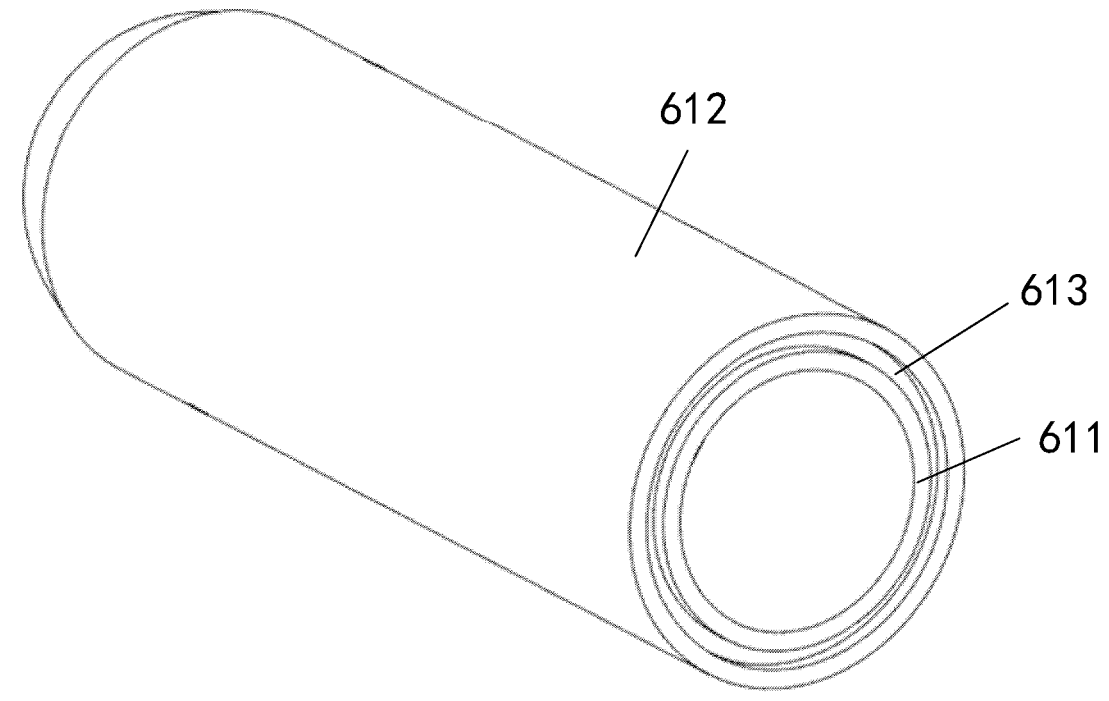

FIG. 6A and FIG. 6B show a structure diagram of the end instrument 600 according to other embodiments of the present disclosure, wherein FIG. 6A is a front view of the end instrument 600, and FIG. 6B is a rear view of the end instrument 600. As shown in FIG. 6A and FIG. 6B, the end instrument 600 may include a first electrode 611 and a second electrode 612. In some embodiments, the first electrode 611 may be formed as a roughly hollow round-headed cylindrical shape, and the second electrode 612 is formed as a roughly annular cross-section and surrounds at least a portion of the first electrode 611 at an interval in a radial direction. In some embodiments, the end instrument 600 may further include an insulating body 613 disposed between the first electrode 611 and the second electrode 612. Similar to the insulating body 513, the insulating body 613 may be made of an insulating material such as plastics, ceramics or mica.

Figure 7:
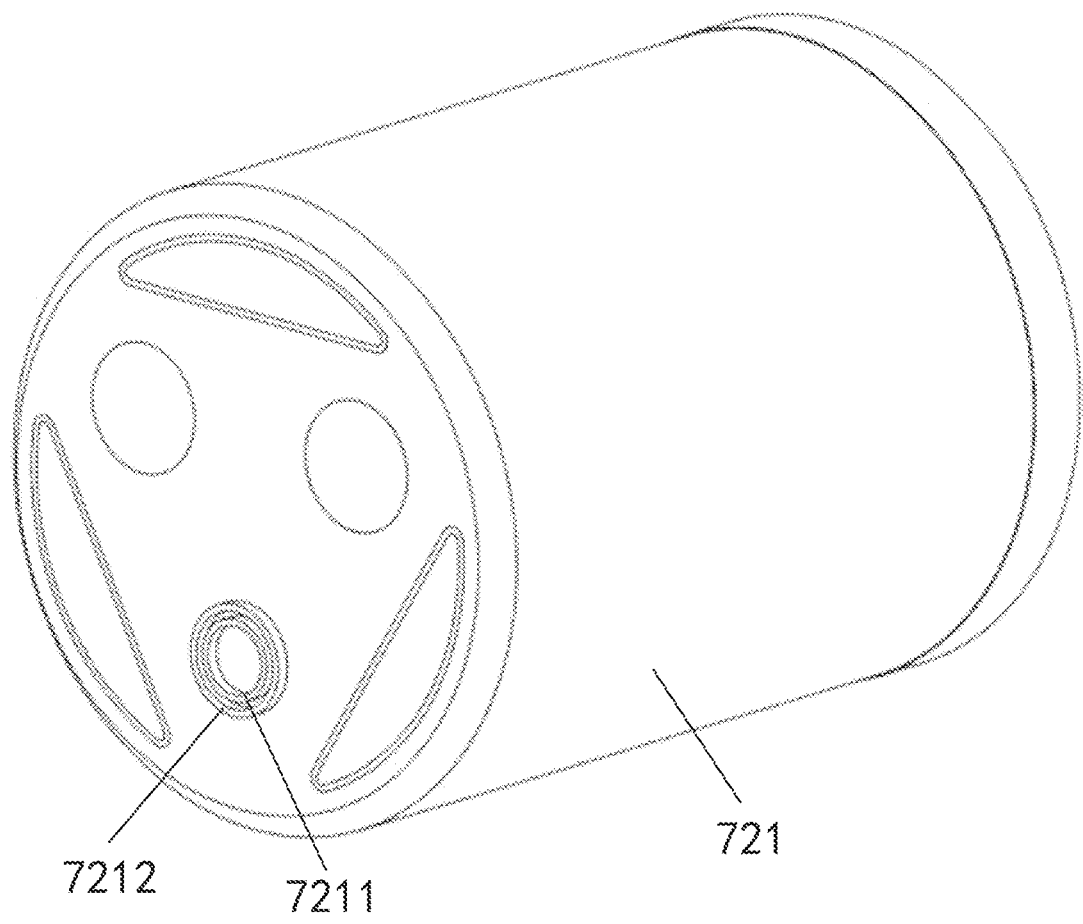
FIG. 7 shows a structure diagram of an endoscope main body according to some embodiments of the present disclosure.

In some embodiments, the endoscope main body is formed with a mounting structure for mounting the end instrument. FIG. 7 shows a structure diagram of an endoscope main body 721 according to some embodiments of the present disclosure. As shown in FIG. 7, the endoscope main body 721 may include an inner annular member 7211 and an outer annular member 7212 for mounting the end instrument (e.g., the end instrument 260 shown in FIG. 2 and FIG. 3, the end instrument 460 shown in FIG. 4, the end instrument 500 shown in FIG. 5 or the end instrument 600 shown in FIG. 6A and FIG. 6B). For example, the first electrode 611 of the end instrument 600 may be mounted onto the inner annular member 7211 of the endoscope main body 721, and the second electrode 612 may be mounted onto the outer annular member 7212. In some embodiments, the inner annular member 7211 or the outer annular member 7212 may be provided with a threaded or snap-in structure, the first electrode 611 or the second electrode 612 of the end instrument 600 may be mounted onto the inner annular member 7211 and the outer annular member 7212 by means of a threaded connection or a snap-in connection. It should be understood that the mounting structure on the main body is not limited to the above structure, any of structures of the end instrument that can enable the mounting does not depart from the scope of the present disclosure. For example, the inner annular member 7211 and the outer annular member 7212 may also be an annular groove recessed from the end surface of the endoscope main body 721.

Figure 8:
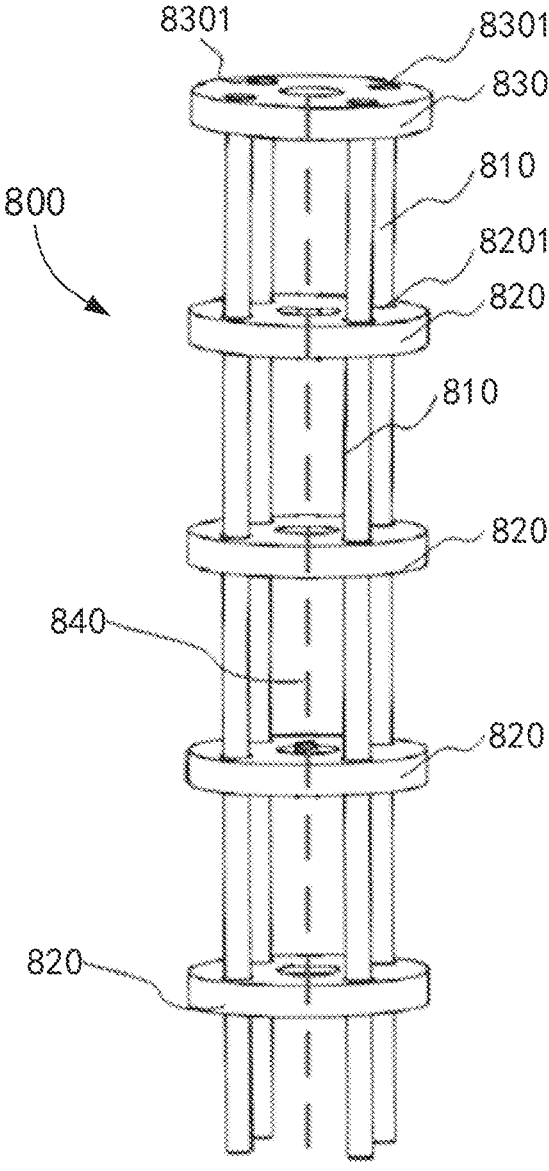
FIG. 8 shows a structure diagram of a segment of an operating arm according to some embodiments of the present disclosure.

FIG. 8 shows a structure diagram of a segment 800 of an operating arm 210 according to some embodiments of the present disclosure. In some embodiments, the operating arm 210 may include at least one segment 800. The segment 800 includes one or more structural bones 810, a fixation disc 830 and at least one spacer disc 820. The structural bone 810 passes through at least one spacer disc 820 and its end is fixedly connected to the fixation disc 830. The spacer disc 820 and the fixation disc 830 is arranged at an interval in the axial direction of the structural bone 810. The spacer disc 820 is provided with a vias 8201 for the structural bone 810 to pass through, and the fixation disc 830 is provided with a fixation hole 8301 that may be used to fix the structural bone 810. An end of the structural bone 810 may be connected to the fixation disc 830, and a proximal end of the structural bone 810 may be connected to a drive mechanism not shown. When the structural bone 810 is driven by the drive mechanism, the structural bone 810 may be moved along the vias 8201. In some embodiments, at least one spacer disc 820 may form a continuum structure, for example a corrugated pipe. In some embodiments, the exterior of the segment 800 may be wrapped with an overlay or an envelope.

In some embodiments, the number of structural bones 810 is one or more, and the structural bones are uniformly or non-uniformly arranged across the cross-section of the spacer disc, for example, located in a central position or arranged along the circumferential direction. In some embodiments, the number of spacer discs 820 is one or more. One or more vias 8201 may be provided on the cross-section of the spacer disc 820, and the shape of the vias 8201 matches or substantially matches the shape of the cross-section of structural bone, such that the structural bone 810 can pass through the vias 8201. In some embodiments, the number of vias 8201 provided on the cross-section of the spacer disc 820 is consistent with the number of structural bones 810, so that each vias 8201 may allow one structural bone 810 to pass through. In some embodiments, the cross-section of the spacer disc 820 is in a circular shape, the vias

8201 on the spacer disc is a circular hole, and the cross-section of the structural bone 810 is circular. In other embodiments, the cross-section of the spacer disc 820 is in a rectangle shape, the vias on the spacer disc is a polygon hole, and the cross-section of the structural bone is polygon and so on.

In some embodiments, the operating arm 210 may further include a plurality of segments 800 connected in series. For example, the arm body 210 may include two segments connected in series, a spacer disc 820 of a segment located at a distal end may be used as a fixation disc of a segment located at a proximal end. By disposing two or more segments 800, a bending flexibility of the arm body 210 may be increased.

In some embodiments, the main body of the endoscope (e.g., the endoscope main body 221 shown in FIG. 2 and FIG. 3, the endoscope main body 421 shown in FIG. 4 or the endoscope main body 721 shown in FIG. 7) may be disposed at the distal end of the operating arm 210. For example, the main body may be fixedly mounted on the fixation disc 830 of the segment 800, and the main body may follow a movement of the distal end of the operating arm.

Figure 9:
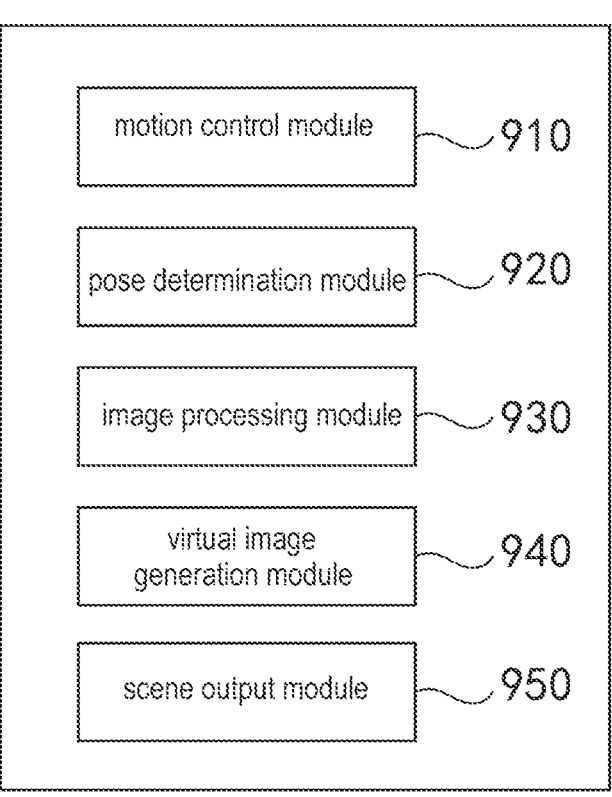
FIG. 9 shows a schematic block diagram of a control device according to some embodiments of the present disclosure.

In the present disclosure, the robot system may further include a control device for implementing a control of the robot system based on an endoscope control method. FIG. 9 shows a structural block diagram of a control device 900 according to some embodiments of the present disclosure. As shown in FIG. 9, the control device 900 may include a motion control module 910, a pose determination module 920, an image processing module 930, a virtual image generation module 940, and a scene output module 950. The motion control module 910 may be used to receive the input motion control instruction to drive the operating arm 210. In some embodiments, the motion control module 910 may be communicatively connected with the control device 120 shown in FIG. 1, receive a motion control instruction input by an operator via the master manipulator, and transmit a drive signal to a drive device to drive the operating arm 210. In some embodiments, the pose determination module 920 may determine, based on a target pose of the end of the operating arm 210 corresponding to a pose of the master manipulator, a pose of the end of the operating arm 210, and further determine poses of the endoscope main body 221 and the first imaging unit 230, the second imaging unit 240 and the end instrument 260 disposed on the endoscope main body 221. In some embodiments, the pose determination module 920 may also receive a signal from a pose sensor such as an electromagnetic pose sensor or an optical fiber sensor, etc., to determine the poses of the operating arm 210 and the endoscope main body 221. The image processing module 930 may be configured to receive a first image from the first imaging unit (e.g., the first imaging unit 230 shown in FIG. 2 or the first imaging unit 430 shown in FIG. 4) and a second image from the second imaging unit (e.g., the second imaging unit 240 shown in FIG. 2 or the second imaging unit 440 shown in FIG. 4), and generate a composite scene image and an actual scene image based on the first image and the second image. The virtual image generation module 940 may be used to generate a virtual image of the end instrument (e.g., the end instrument 260 shown in FIG. 2 and FIG. 3, the end instrument 460 shown in FIG. 4, the end instrument 500 shown in FIG. 5 or the end instrument 600 shown in FIG. 6A and FIG. 6B) in the composite scene image. The scene output module 950 may switch between outputting the composite scene image with the virtual image and outputting the actual scene image to the display device according to instructions, or simultaneously output the composite scene image with the virtual image and the actual scene image to the display device. It should be understood that the control device of the present disclosure include, but are not limited to, the above structures, any of the control devices that can implement the robot system does not depart from the scope of the present disclosure.

In some embodiments, the robot system may further include a display device (e.g., the display device 1200 shown in FIG. 12) for displaying an image based on an instruction output by the control device 900.

Some embodiments of the present disclosure provide an endoscope control method. FIG. 10 shows a flowchart of an endoscope control method 1000 according to some embodiments of the present disclosure. In some embodiments, part or all of the steps in the method 1000 may be performed by the control device (e.g., the control device 900 shown in FIG. 9 or the control device 1970 shown in FIG. 19) of the robot system (e.g., the robot system 100 shown in FIG. 1 or the robot system 1900 shown in FIG. 19). The control device may include a computing device. The method 1000 may be implemented by software, firmware and/or hardware. In some embodiments, the method 1000 may be implemented as computer-readable instructions. These instructions may be read and executed by a general-purpose processor or a dedicated processor (e.g., the control device 1970 shown in FIG. 19). In some embodiments, these instructions may be stored on a computer-readable medium.

Referring to FIG. 10, at step 1001, the endoscope is controlled to move. The endoscope may include a main body, a first imaging unit, a second imaging unit and an end instrument protruding from the end of the main body. In some embodiments, in response to the motion control instruction input by an operator via a master manipulator, a drive signal may be transmitted to the drive device to drive the motion arm or the operating arm, thereby controlling the motion of the endoscope. In some embodiments, a target pose of the end of the operating arm may be determined based on a master-slave motion mapping relationship between a pose of the master manipulator and a pose of the end of the operating arm according to the pose of the master manipulator, and the drive signal for controlling the motion of the endoscope may be determined based on a current pose and the target pose of the end of the operating arm. In some embodiments, the step 1001 may be performed by the control device 900 (e.g., the motion control module 910).

Continuing with reference to FIG. 10, at step 1003, a first image is obtained from the first imaging unit. In some embodiments, the first imaging unit is configured to be located on one side of the main body of the endoscope with respect to the end instrument. During the movement of the endoscope within the scene, the first imaging unit continuously takes the first images in a first field of view, and the control device 900 (e.g., an image processing module 930) may receive the first images from the first imaging unit. In some embodiments, the end instrument is located in the first field of view of the first imaging unit, and the first image comprises an image of the end instrument taken from the one side of the main body.

Continuing with reference to FIG. 10, at step 1005, a second image is obtained from the second imaging unit, wherein the first image and the second image have different fields of view and include images of the end instrument. In some embodiments, the second imaging unit is configured to be located on the other side of the main body of the endoscope with respect to the end instrument. During the movement of the endoscope within the scene, the second imaging unit continuously takes the second images in a second field of view different from the first field of view of the first imaging unit, and the control device 900 (e.g., the image processing module 930) may receive the second images from the second imaging unit. In some embodiments, the end instrument is located in the second field of view of the second imaging unit, and the second image comprises an image of the end instrument taken from the other side of the main body.

Continuing with reference to FIG. 10, at step 1007, a composite scene image is generated based on the first image and the second image, to remove an actual image of the end instrument. In the present disclosure, due to the occlusion of the end instrument, the first imaging unit and the second imaging unit each can not photograph the entire scene. In some embodiments, the control device 900 (e.g., the image processing module 930) may use one of the first image or the second image to fill a portion of the other image that is blocked by the end instrument through a computer vision processing, thereby generating a two-dimensional composite scene image or a three-dimensional composite scene image with the end instrument being removed. For example, an exemplary method of generating the composite scene image based on the first image and the second image may include a method 1400 as shown in FIG. 14. In some embodiments, the computer vision processing may include a feature point detection algorithm, which may extract feature points in the first image and the second image for matching, thereby enabling a two-dimensional stitching of the first image and the second image. In some embodiments, the computer vision processing may include an image sequence optical flow reconstruction algorithm, which may determine a depth of a pixel in the scene space based on an optical flow of the pixel in the image, thereby enabling a three-dimensional reconstruction of the scene. By generating the composite scene image, a more complete image of the scene, which is at least partially unblocked by the end instrument, can be displayed on the display device, thereby facilitating the operator to observe a lumen and an operating area without hindrance.

Continuing with reference to FIG. 10, at step 1009, a virtual image of the end instrument is generated in the composite scene image. For example, an exemplary method of generating the virtual image of the end instrument in the composite scene image may include a method 1700 as shown in FIG. 17. In some embodiments, the control device 900 (e.g., a virtual image generation module 940) may generate the virtual image of the end instrument at a position corresponding to the end instrument in the composite scene image by a real-time rendering method. By generating the virtual image of the end instrument in the composite scene image, the operator can be reminded with an actual position and size of the end instrument without hindering the operator from observing the scene, so as to avoid colliding with a wall surface of the lumen or the operating area due to the inability to see the end instrument during operation.

In some embodiments, the method 1000 may further include scene mode switching based on a display mode instruction. FIG. 11 shows a flowchart of a method 1100 of displaying a scene image based on a display mode instruction according to some embodiments of the present disclosure. In some embodiments, part or all of the steps in the method 1100 may be performed by the control device (e.g., the control device 900 shown in FIG. 9 or the control device 1970 shown in FIG. 19) of the robot system (e.g., the robot system 100 shown in FIG. 1 or the robot system 1900 shown in FIG. 19). The control device may include a computing device. The method 1100 may be implemented by software, firmware and/or hardware. In some embodiments, the method 1100 may be implemented as computer-readable instructions. These instructions may be read and executed by a general-purpose processor or a dedicated processor (e.g., the control device 1970 shown in FIG. 19). In some embodiments, these instructions may be stored on a computer-readable medium.

With reference to FIG. 11, at step 1101, an actual scene image is generated based on the first image and/or the second image to display an actual image of the end instrument. In some embodiments, the first image taken by the first imaging unit or the second image taken by the second imaging unit may be used as a two-dimensional actual scene image, which comprises the actual image of the end instrument. In some embodiments, the control device 900 (e.g., the image processing module 930) may generate a three-dimensional actual scene image by a computer vision algorithm based on the first image or the second image. For example, an exemplary method of generating the three-dimensional actual scene image based on the first image or the second image may include a method 1600 as shown in FIG. 16. In some embodiments, the computer vision algorithm may include an image sequence optical flow reconstruction algorithm, which may determine a depth of a pixel in the scene space based on an optical flow of the pixel in the first image or the second image, thereby enabling a three-dimensional reconstruction of the actual scene. In some embodiments, two actual scene images with different fields of view may also be generated simultaneously based on the first image and the second image, for being displayed side by side on the display device.

Continuing with reference to FIG. 11, at step 1103, the composite scene image with the virtual image of the end instrument and/or the actual scene image is displayed in response to the display mode instruction. The display mode instruction may include, for example, at least one of a motion control instruction, an end instrument operation instruction and a display mode selection instruction.

The motion mode instruction is used to control the movement of the endoscope in the lumen. In some embodiments, the motion control instruction for controlling the motion of the endoscope may include a first endoscope motion instruction, and the first endoscope motion instruction may include a feed instruction for controlling the endoscope to feed or a steering instruction for controlling the endoscope to steer. In some embodiments, the first endoscope motion instruction may be determined based on a master-slave motion mapping relationship between a pose of the master manipulator and a pose of the end of the arm body according to the pose of the master manipulator, and the first endoscope motion instruction may be, for example, a target pose of the end of the operating arm of the endoscope or a drive signal associated with the target pose. In some embodiments, the method 1100 may further include displaying, in response to the first endoscope motion instruction, a composite scene image with a virtual image of the end instrument, and controlling, based on the first endoscope motion instruction, the endoscope to move towards the operating area. For example, the first endoscope motion instruction may be determined based on the operation of the operator on the master manipulator, a scene output module 950 of the control device 900 may output, in response to the first endoscope motion instruction, the composite scene picture with the virtual image of the end instrument to the display device for display, and a motion control module 910 of the control device 900 may control the endoscope to feed or steer based on the first endoscope motion instruction. By displaying the composite scene image with the end instrument removed, it can be avoided that the operator operates the endoscope to feed or steer in an incomplete field of view, thus undertaking an unnecessary surgical risk.

The end instrument operation instruction may be used to control an operation of the end instrument. In some embodiments, the method 1100 may further include displaying, in response to the end instrument operation instruction, the actual scene image, or displaying, in response to the termination of the end instrument operation instruction, the composite scene image with the virtual image of the end instrument. In some embodiments, the end instrument operation instruction may include an activation instruction for the end instrument, and the activation instruction is used to instruct to start the operation of end instrument. In the case that the end instrument is an electrocoagulation hemostatic device (e.g., the end instrument 500 shown in FIG. 5 or the end instrument 600 shown in FIG. 6A and FIG. 6B), the activation instruction may be, for example, turning on a power supply. In some embodiments, the scene output module 950 of the control device 900 may in response to the end instrument operation instruction, display the actual scene image or switch the displayed picture from the composite scene image with the virtual image of the end instrument to the actual scene image, thereby allowing the operator to perform surgical tasks in the case of observing the end instrument, facilitating to improve accuracy of the operation. The termination of the end instrument operation instruction means that the operator completes or temporarily discontinues the operation of the end instrument. In the case that the end instrument is the electrocoagulation hemostatic device (e.g., the end instrument 500 shown in FIG. 5 or the end instrument 600 shown in FIG. 6A and FIG. 6B), the termination of the end instrument operation instruction may be, for example, turning off the power supply. In some embodiments, the scene output module 950 of the control device 900 may in response to the termination of the end instrument operation instruction, display the composite scene image with the virtual image of the end instrument or switch the displayed picture from the actual scene image to the composite scene image with the virtual image of the end instrument, thereby allowing the operator to confirm the effect of the surgical tasks in a full field of view. In some embodiments, the end instrument operation instruction may have a higher priority in display mode control than the first endoscope motion instruction. In this way, when the end instrument is triggered to start operating, the operator can more intuitively see an actual situation in the body.

Those skilled in the art will appreciate that, in the present disclosure, the display mode control priority refers that in the presence of a plurality of display mode instructions simultaneously, a display mode instruction with a higher priority has a higher control priority. In some embodiments, the operator may at the same time of issuing the end instrument operation instruction, control the endoscope to feed or steer by the first endoscope motion instruction, to achieve a first composite operation of controlling the motion of the endoscope when activating the end instrument for operation. For example, in the case that the end instrument is the electrocoagulation hemostatic device, the operator may control the endoscope to feed while activating the electrocoagulation hemostatic device, so as to achieve the slight contact and press of the electrocoagulation hemostatic device on the tissue. By displaying the actual scene images preferentially based on the end instrument operation instruction, it can be ensured that the operator performs surgical tasks based on the actual situation in the body. Similarly, for other composite operations containing a variety of operations, the display modes can also be controlled based on the display mode control priority of various operations or operation instructions.

In some embodiments, the motion control instruction for controlling the motion of the endoscope may further include a second endoscope motion instruction, which may include controlling the endoscope to move away from the operating area. For example, the second endoscope motion instruction may be a retreat instruction. In some embodiments, the endoscope motion instruction may be determined based on a master-slave motion mapping relationship between a pose of the master manipulator and a pose of the end of the operating arm according to the pose of the master manipulator, and the endoscope motion instruction may be, for example, a target pose of the end of the operating arm of the endoscope or a drive signal associated with the target pose.

In some embodiments, the method 1100 may further include controlling, based on the second endoscope motion instruction, the endoscope to move away from the operating area, and displaying, in response to a distance of the endoscope away from the operating area exceeding a threshold, the composite scene image with the virtual image of the end instrument. The distance of the endoscope away from the operating area exceeding the threshold may include determining whether the distance for which the endoscope retreats exceeds a threshold, or determining whether a cumulative value of an amount of position change of the master manipulator used for controlling the motion of the endoscope exceeds a threshold, wherein the amount of position change corresponds to the second endoscope motion instruction (e.g., the retreat instruction). For example, in a plurality of control loops, the retreat instruction proportional to the amount of position change of the master manipulator may be determined based on the operation of the operator on the master manipulator. The motion control module 910 of the control device 900 may control the endoscope to move away from the operating area based on the retreat instruction, and the control device 900 may obtain the amount of change (e.g., stored to memory) in retreat position of the master manipulator in each control cycle, and accumulate these amounts of position change. When the accumulated value of the amount of position change exceeds a predetermined threshold, the scene output module 950 of the control device 900 may display the composite scene image with the virtual image of the end instrument or switch the displayed picture from the actual scene image to the composite scene image with the virtual image of the end instrument, so as to facilitate the operator's observation, thus avoiding injury to internal organs or lumens during the retreat process. This display operation for the second endoscope motion instruction can has higher priority in display mode control than other motion control instructions and the end instrument operation instruction and the like. In this way, when the operator has an intention to withdraw the endoscope, the display mode can be automatically adjusted in time, facilitating the operator to observe the situation in the body.

In some embodiments, the operator may at the same time of issuing the end instrument operation instruction, control the endoscope to withdraw by the second endoscope motion instruction, to achieve a second composite operation of controlling the motion of the endoscope when activating the end instrument for operation. For example, in the case where the end instrument is the clamp-type device, the operator may at the same time of activating the clamp-type device to clamp a tissue, control the endoscope to retreat, to achieve a slight traction and peeling of the clamp-type device to the tissue. By displaying the actual scene image based on the end instrument operation instruction when the distance of the endoscope away from the operating area is below a threshold, and displaying the composite scene image with the virtual image of the end instrument preferentially based on the second endoscope motion instruction when the distance of the endoscope away from the operating area exceeds the threshold, an actual or full field of view in the body can be automatically provided to the operator for easy observation. In some embodiments, the method 1100 may further comprise terminating, in response to the distance of the endoscope away from the operating area exceeding the threshold, the end instrument operation instruction. In this way, the end instrument can be prevented from injuring the internal organs or lumens during the retreat process of the endoscope.

In some embodiments, the motion control instruction for controlling the motion of the endoscope may further include an automatic exit instruction which may be used to control the endoscope to automatically exit from the human body. In some embodiments, the method 1100 may further include controlling the endoscope to exit from the human body based on the automatic exit instruction, and displaying the composite scene image with the virtual image of the end instrument in response to the automatic exit instruction. The automatic exit instruction may allow the operator to withdraw the endoscope quickly. Similarly, the automatic exit instruction may has higher priority in display mode control than other motion control instructions (e.g., the first endoscope motion instruction, the second endoscope motion instruction, etc.) and the end instrument operation instruction. In addition, the automatic exit instruction may automatically terminate other motion control instructions and the end instrument operation instruction that are being executed, and may disable other motion control instructions, the end instrument operation instruction or a display mode selection instruction. Alternatively, the automatic exit instruction can also allow the display mode selection instruction to be triggered during execution, so as to facilitate the operator switch the display mode and better observe the situation in the body.

The display mode selection instruction can be used to manually trigger the switch of the display mode, for example, through a manual input by the operator. In some embodiments, the display mode selection instruction may include at least one of a composite scene display instruction, an actual scene display instruction and a multi-scene display instruction. Among them, the composite scene display instruction is used to display the composite scene image with the virtual image of the end instrument, the actual scene display instruction is used to display the actual scene image, and the multi-scene display instruction is used to display the composite scene image with the virtual image of the end instrument and the actual scene image simultaneously. For example, the multi-scene display instruction may be used to display at least a portion of the actual scene image in a first window of the display device, and display at least a portion of the composite scene image with the virtual image of the end instrument in a second window of the display device.

In some embodiments, the display mode selection instruction may has higher priority in display mode control than other display mode instructions (such as the first endoscope motion instruction, the second endoscope motion instruction, the end instrument operation instruction and the automatic exit instruction and the like). Since the display mode selection instruction needs to be triggered by the operator, expressing a direct display demand of the operator, it has a high priority in the operation.

FIG. 12 shows a schematic diagram of a multi-scene display on a display device 1200 according to some embodiments of the present disclosure. As shown in FIG. 12, in some embodiments, the display device 1200 may include a first window 1210 and a second window 1220, and the first window 1210 encloses the second window 1220 from the outside, forming a so-called picture-in-picture display mode. In some embodiments, at least a portion of the actual scene image may be displayed in the first window 1210, and at least a portion of the composite scene image with the virtual image of the end instrument may be displayed in the second window 1220. For example, the scene output module 950 of the control device 900 may in response to the multi-scene display instruction, simultaneously output the actual scene image and the composite scene image with the virtual image of the end instrument to the display device 1200. The display device 1200 may display a portion of the actual scene image in the first window 1210, and display in the second window 1220, for example, a surgical site in the composite scene image with the virtual image of the end instrument. Such way of displaying allows the operator to see both the environment around the endoscope and the surgical site located in front of the end instrument simultaneously, which can improve the accuracy of the operation while suppressing a discomfort of the operator caused by repeated image switching. It should be understood that the way of presenting two scene images simultaneously on the display device includes, but is not limited to, the above described way. For example, the display device 1200 may also display the first window 1210 and the second window 1220 side by side in a form of left and right split screens.

Some embodiments of the present disclosure provide a method of generating a composite scene image based on a first image and a second image. FIG. 13 shows a flowchart of a method 1300 of generating a composite scene image based on a first image and a second image according to some embodiments of the present disclosure. In some embodiments, part or all of the steps in the method 1300 may be performed by the control device (e.g., the control device 900 shown in FIG. 9, the control device 1970 shown in FIG. 19) of the robot system (e.g., the robot system 100 shown in FIG. 1 or the robot system 1900 shown in FIG. 19). The control device may include a computing device. The method 1300 may be implemented by software, firmware and/or hardware. In some embodiments, the method 1300 may be implemented as computer-readable instructions. These instructions may be read and executed by a general-purpose processor or a dedicated processor (e.g., the control device 1970 shown in FIG. 19). In some embodiments, these instructions may be stored on a computer-readable medium.

Referring to FIG. 13, at step 1301, a supplementary image is determined based on the first image or the second image. The supplementary image includes a portion of the second image or the first image that is blocked by the end instrument. In some embodiments, the supplementary image may be determined based on the first image, and the supplementary image comprises a portion of the second image that is blocked by the end instrument. For example, as shown in FIG. 4, the first imaging unit 430 may take the first image in the first field of view (e.g., a sum of the field of view 431 and the field of view 432). The first image includes a first environment image (e.g., an image of a lumen wall surface) within the field of view 431 and an image of the end instrument 460 located within the field of view 432. The first environment image may include an image within a field of view 431' (a part of the field of view 431), and the image is a supplementary image for synthesis with the second image taken by the second imaging unit 440, and corresponds to the portion of the second image that is blocked by the end instrument 460. Similarly, in some embodiments, the supplementary image may be determined based on the second image, and the supplementary image comprises a portion of the first image that is blocked by the end instrument. For example, the second imaging unit 440 may take the second image in the second field of view (e.g., a sum of the field of view 441 and the field of view 442). The second image includes a second environment image (e.g., an image of a lumen wall surface) within the field of view 441 and an image of the end instrument 460 located within the field of view 442. The second environment image may include an image within a field of view 441' (a part of the field of view 441), and the image is a supplementary image for synthesis with the first image taken by the first imaging unit 430, and corresponds to the portion of the first image that is blocked by the end instrument 460.

In some embodiments, a position of the supplementary image in the first image or a position of the supplementary image in the second image may be determined based on a spatial positional relationship between the first imaging unit 430, the second imaging unit 440 and the end instrument 460, thereby separating the supplementary image from the first image or the second image. The supplementary image may be used to stitch the second environment image in the second image or the first environment image in the first image to generate a stitched image.

Continuing with reference to FIG. 13, at step 1303, the first environment image or the second environment image are determined based on the first image or the second image. The first environment image and the second environment image do not include the image of the end instrument. In some embodiments, the image of the end instrument 460 may be removed from the first image or the second image based on a difference between the environment image and the image of the end instrument 460, obtaining the first environment image in the first image or the second environment image in the second image. For example, the image of the end instrument 460 may be removed from the first image or the second image based on color features, boundary features, texture features or spatial relationship features, to generate the first environment image or the second environment image.

Continuing with reference to FIG. 13, at step 1305, the first environment image or the second environment image and the supplementary image are stitched to generate the stitched image. Stitching the first environment image and the supplementary image to generate the stitched image is described as an example below, but it should be understood that it is also possible to generate the stitched image by stitching the second environment image and the supplementary image.

In some embodiments, a feature point detection algorithm may be used to extract feature points from the first environment image and the supplementary image respectively. The feature point detection algorithm may be any one of a Harris (corner detection) algorithm, a SIFT (Scale Invariant Feature Transform) algorithm, a SURF (Speeded-Up Robust Features) algorithm or an ORB (Oriented Fast and Rotated Brief, feature descriptor) algorithm. For example, the feature point detection algorithm can extract the feature points from the edges of the first environment image and the supplementary image respectively, and establish a feature point database of the image according to a data structure of the feature points. The data structure of the feature points may include a location coordinate, a scale, a direction and a feature vector of the feature points.

In some embodiments, a feature matching algorithm may be used to perform a feature matching on the feature points of the edges of the first environment image and the supplementary image, thereby determining a correlation between the edge of the first environment image and the edge of the supplementary image. The feature matching algorithm may be any one of a brute force matching algorithm, a cross-matching algorithm, a KNN (k-nearest neighbor classification) matching algorithms, a RANSAC (Random Sample Consensus) matching algorithm.

In some embodiments, a registration image may be generated based on the first environment image and/or the supplementary image. For example, a transformation relationship between a first image coordinate system and a second image coordinate system may be determined based on the spatial positional relationship between the first imaging unit 430 and the second imaging unit 440, and the supplementary image in the second image coordinate system is converted into an image in the first image coordinate system based on this transformation relationship, generating the registration image for image fusion with the first environment image. In some embodiments, it may also be possible to covert the first environment image and the supplementary image into an image under the reference coordinate system based on a transformation relationship between the first image coordinate system, the second image coordinate system and a reference coordinate system (e.g., a coordinate system of the end of the main body of the endoscope).

In some embodiments, the stitched image may be generated by stitching the first environment image and the registration image. For example, the edges of the first environment image and the registration image can be aligned and stitched based on successful matched feature points in the first environment image and the supplementary image, thereby generating the stitched image. In some embodiments, the resulting stitched image may be a two-dimensional stitched image. In some embodiments, the two-dimensional stitched image may be used as a two-dimensional composite scene image.

In some embodiments, the method 1300 may further include further processing the first environment image, the second environment image, the supplementary image or the stitched image to generate a three-dimensional composite scene image. FIG. 14 shows a flowchart of a method 1400 of generating a three-dimensional composite scene image based on a first image and a second image according to some embodiments of the present disclosure. In some embodiments, part or all of the steps in the method 1400 may be performed by the control device (e.g., the control device 900 shown in FIG. 9 or the control device 1970 shown in FIG. 19) of the robot system (e.g., the robot system 100 shown in FIG. 1 or the robot system 1900 shown in FIG. 19). The control device may include a computing device. The method 1400 may be implemented by software, firmware and/or hardware. In some embodiments, the method 1400 may be implemented as computer-readable instructions. These instructions may be read and executed by a general-purpose processor or a dedicated processor (e.g., the control device 1970 shown in FIG. 19). In some embodiments, these instructions may be stored on a computer-readable medium.

Referring to FIG. 14, at step 1401, for at least one of the first environment image, the second environment image, the supplementary image or the stitched image, an optical flow field of the image is determined based on the image and a previous frame image of the image (two consecutive frame images). The optical flow field comprises optical flows of a plurality of pixels in the image. The first environment image in the first image is described as an example below.

In some embodiments, during the movement of the endoscope (e.g., the endoscope 420) within the lumen, the first imaging unit (e.g., the first imaging unit 430) photographs a lumen environment in continuously varying fields of view (corresponding to a direction of an optical axis), to obtain a plurality of first images arranged in accordance with a frame sequence. The first environment image may be determined by removing the image of the end instrument (e.g., the end instrument 460) from the first image. The method of determining the first environment image may be achieved similarly to the step 1303 in the method 1300.

A pixels in the first environment image corresponds to object points in the environment, and in the sequence of the first environment images, the pixel moves between adjacent frames (for example, a previous frame and a current frame of the images) to produce an optical flow, wherein the optical flow is a two-dimensional vector used to describe a position change of the pixel, corresponds to a three-dimensional motion vector of the object point in the environment, and is a projection of the three-dimensional motion vector of the object point on an image plane. In some embodiments, the optical flows of the pixels in the first environment image may be calculated through the previous frame and the current frame of the first environment images. In some embodiments, by calculating the optical flows of a plurality of pixels in the first environment image, an optical flow field of the first environment image can be obtained. The optical flow field is an instantaneous velocity field generated by the movement of the pixels of the first environment image on the image plane, and includes instantaneous motion vector information of the pixel, such as a direction of motion and a speed of motion of the pixel.

Continuing with reference to FIG. 14, at step 1403, a depth map of the image is generated based on the optical flow field of the image and the pose of the imaging unit corresponding to the image. The depth map comprises depths of the object points corresponding to the plurality of pixels. In some embodiments, a depth value of the object point in the lumen environment corresponding to the pixel may be determined based on the optical flow of the pixel in the optical flow field of the first environment image and a change of the pose of the first imaging unit, thereby generating the depth map of the first environment image based on the depth of the object point. For example, an exemplary method of generating the depth map of the image based on the optical flow field and the pose of the imaging unit may include a method 1500 as shown in FIG. 15.

FIG. 15 shows a flowchart of a method 1500 of generating a depth map based on an optical flow field and a pose of an imaging unit according to some embodiments of the present disclosure. In some embodiments, part or all of the steps in the method 1500 may be performed by the control device (e.g., the control device 900 shown in FIG. 9 or the control device 1970 shown in FIG. 19) of the robot system (e.g., the robot system 100 shown in FIG. 1 or the robot system 1900 shown in FIG. 19). The control device may include a computing device. The method 1500 may be implemented by software, firmware and/or hardware. In some embodiments, the method 1500 may be implemented as computer-readable instructions. These instructions may be read and executed by a general-purpose processor or a dedicated processor (e.g., the control device 1970 shown in FIG. 19).

In some embodiments, these instructions may be stored on a computer-readable medium.

Referring to FIG. 15, at step 1501, a focus of the optical flow field is determined based on the optical flow field of the image. For example, when generating the optical flow field based on the first environment image, in the case where the endoscope feeds or retreats, the optical flows of a plurality of pixels in the first environment image are not parallel to each other, and an extension line of an optical flow vector converges on the focus of the optical flow field, which is a fixed point in the optical flow field. In some embodiments, the optical flow vector in the optical flow field may have a correspondence with the focus, and each optical flow vector may separately converge to a different focus. In some embodiments, for example, when the endoscope feeds, the focus of the optical flow field may include a Focus of expansion (FOE), and the POE is a convergence point of the reverse extension of the optical flow vectors. In some embodiments, for example, when the endoscope retreats, the focus of the optical flow field may include a Focus of contraction (FOC), and the FOC is a convergence point of the forward extension of the optical flow vectors.

Continuing with reference to FIG. 15, at step 1503, distances between the plurality of pixels and the focus are determined based on the focus of the optical flow field. For example, in the first environment image, the distance between each of the plurality of pixels and the focus may be determined in the first image coordinate system.

Continuing with reference to FIG. 15, at step 1505, velocities of the plurality of pixels in the optical flow field are determined based on the optical flow field of the image. The velocity of the optical flow of the pixel may be a ratio of a distance (a length of the optical flow) for which the pixel moves in the optical flow field to a time interval of two consecutive frames. In some embodiments, in the first environment image, the distance for which each of the plurality of pixels moves in the optical flow field may be determined in the first image coordinate system. In some embodiments, the time interval between two consecutive frames (time per frame) may be, for example, 1/60 second, but not limited thereto, it may be appropriately adjusted according to imaging requirements.

Continuing with reference to FIG. 15, at step 1507, a velocity of the imaging unit is determined based on the pose of the imaging unit corresponding to the image. In some embodiments, the first image coordinate system and the coordinate system of the end of the main body of the endoscope have a predetermined transformation relationship, and a pose of the first imaging unit may be calculated based on a pose of the end of the main body. In some embodiments, a distance for which the first imaging unit moves may be determined based on the pose of the first imaging unit, thereby the velocity of the first imaging unit is determined based on the distance for which the first imaging unit moves and the time interval of two consecutive frames.

Continuing with reference to FIG. 15, at step 1509, the depth map of the image is determined based on the distances between the plurality of pixels and the focus, the velocities of the plurality of pixels in the optical flow field and the velocity of the imaging unit. In some embodiments, in the optical flow field generated from the first environment image, a depth value (depth information) of the object point may be determined based on the distance between one pixel and the focus, the velocity of the pixel in the optical flow field and the velocity of the first imaging unit. The depth value of the object point may be a distance from the object point to the image plane of the first imaging unit. The depth map of the first environment image may be obtained by calculating the depth value of the object point for each pixel in the first environment image.

In some embodiments, it may also be possible to determine the distance for which each of the plurality of pixels moves in the optical flow field based on the optical flow field of the image, and determine the moving distance of the imaging unit based on the pose of the imaging unit corresponding to the image. Thus, the depth map of the image is determined based on the distance between each of the plurality of pixels and the focus, the distance for which each of the plurality of pixels moves in the optical flow field, and the moving distance of the imaging unit.

Continuing with reference to FIG. 14, at step 1405, object point spatial coordinates of the object points corresponding to the plurality of pixels are determined based on the depth map of the image and pixel coordinates of the plurality of pixels. In some embodiments, the object point spatial coordinate of the object point may be determined based on the pixel coordinate of the pixel of the first environment image in the first image coordinate system and the depth value of the object point corresponding to the pixel, thereby realizing the transformation of a two-dimensional pixel in the first environment image to a three-dimensional coordinate.

Continuing with reference to FIG. 14, at step 1407, color information of the plurality of pixels is obtained based on the image. In some embodiments, a color feature extraction algorithm may be used to extract the color information of the pixels in the first environment image. The color feature extraction algorithm can be any one of methods such as a color histogram, a color set, a color moment, a color aggregation vector, and so on.

Continuing with reference to FIG. 14, at step 1409, a point cloud fusion is performed on the image based on the color information of the plurality of pixels and the object point spatial coordinates, to generate a three-dimensional point cloud. In some embodiments, the object point spatial coordinate of the object point may be converted based on an intrinsics matrix of the first imaging unit, and the point cloud fusion is performed on the first environment image based on the color information of the pixels, to generate the three-dimensional point cloud. The three-dimensional point cloud includes three-dimensional spatial coordinates and color information of the object points. In some embodiments, the intrinsics of the first imaging unit may be known or obtained by calibration.

In some embodiments, the method 1400 may be employed to process the first environment image or the second environment image and the supplementary image to generate the three-dimensional point clouds. For example, in some embodiments, a feature extraction and stereo matching may be performed on the three-dimensional point clouds of the first environment image and the supplementary image, to achieve the stitching of the first environment image and the supplementary image, thereby generating a three-dimensional stitched image. In some embodiments, it may also be possible to use the method 1400 to process a registration image generated based on the supplementary image to generate a three-dimensional point cloud, and perform a feature extraction and stereo matching on the three-dimensional point clouds of the first environment image and the registration image, thereby stitching to generate a three-dimensional stitched image. It should be understood that it may also be possible to stitch the second environment image in the second image and a corresponding supplementary image to generate the three-dimensional stitched image.

In some embodiments, the two-dimensional stitched image or the three-dimensional stitched image may be used as the composite scene image. In some embodiments, the two-dimensional composite scene image may also be processed to generate the three-dimensional composite scene image. For example, the method 1400 may be used to process the stitched image generated in the method 1300 to achieve the conversion of the composite scene image from two-dimensional to three-dimensional.

In some embodiments, the method 1100 may further include generating a three-dimensional actual scene image based on at least one of the first image or the second image. FIG. 16 shows a flowchart of a method 1600 of generating a three-dimensional actual scene image based on a first image and/or a second image according to some embodiments of the present disclosure. In some embodiments, part or all of the steps in the method 1600 may be performed by the control device (e.g., the control device 900 shown in FIG. 9 or the control device 1970 shown in FIG. 19) of the robot system (e.g., the robot system 100 shown in FIG. 1 or the robot system 1900 shown in FIG. 19). The control device may include a computing device. The method 1600 may be implemented by software, firmware and/or hardware. In some embodiments, the method 1600 may be implemented as computer-readable instructions. These instructions may be read and executed by a general-purpose processor or a dedicated processor (e.g., the control device 1970 shown in FIG. 19). In some embodiments, these instructions may be stored on a computer-readable medium.

Referring to FIG. 16, at step 1601, for the first image or the second image, the optical flow field of the image is determined based on the image and a previous frame image of the image. The optical flow field comprises optical flows of a plurality of pixels in the image. In some embodiments, the step 1601 may be similarly implemented as the step 1401 in the method 1400.

Continuing with reference to FIG. 16, at step 1603, a depth map of the image is generated based on the optical flow field of the image and the pose of the imaging unit corresponding to the image. The depth map comprises depths of the object points corresponding to the plurality of pixels. In some embodiments, the step 1603 may be similarly implemented as the step 1403 in the method 1400.

Continuing with reference to FIG. 16, at step 1605, object point spatial coordinates of the object points corresponding to the plurality of pixels are determined based on the depth map of the image and pixel coordinates of the plurality of pixels. In some embodiments, the step 1605 may be similarly implemented as the step 1405 in the method 1400.

Continuing with reference to FIG. 16, at step 1607, color information of the plurality of pixels is obtained based on the image. In some embodiments, the step 1607 may be similarly implemented as the step 1407 in the method 1400.

Continuing with reference to FIG. 16, at step 1609, a point cloud fusion is performed on the image based on the image and based on the color information of the plurality of pixels and the object point spatial coordinates, to generate a three-dimensional point cloud. In some embodiments, the step 1609 may be similarly implemented as the step 1409 in the method 1400.

Some embodiments of the present disclosure provide a method of generating a virtual image of the end instrument in a composite scene image. FIG. 17 shows a flowchart of a method 1700 of generating a virtual image of the end instrument in a composite scene image according to some embodiments of the present disclosure. In some embodiments, part or all of the steps in the method 1700 may be performed by the control device (e.g., the control device 900 shown in FIG. 9 or the control device 1970 shown in FIG. 19) of the robot system (e.g., the robot system 100 shown in FIG. 1 or the robot system 1900 shown in FIG. 19). The control device may include a computing device. The method 1700 may be implemented by software, firmware and/or hardware. In some embodiments, the method 1700 may be implemented as computer-readable instructions. These instructions may be read and executed by a general-purpose processor or a dedicated processor (e.g., the control device 1970 shown in FIG. 19). In some embodiments, these instructions may be stored on a computer-readable medium.

Referring to FIG. 17, at step 1701, a position and size of the end instrument in the composite scene image is determined. In some embodiments, the position and size of the end instrument in the composite scene image may be determined based on inherent parameters of the end instrument. The inherent parameters of the end instrument may include a position parameter of the end instrument on the main body (e.g., a relative position relationship with the first imaging unit and the second imaging unit), an orientation parameter and a size parameter. For example, the inherent parameters of the end instrument may be known or obtained by calibration. In some embodiments, it may also be possible to determine, based on the edges of the first environment image, the second environment image or the supplementary image the position and size of the end instrument in the composite scene image.

Continuing with reference to FIG. 17, at step 1703, a virtual image of the end instrument is generated in the composite scene image. In some embodiments, the virtual image of the end instrument may be generated in the composite scene image by real-time rendering. For example, the virtual image of the end instrument may be generated for each frame image of the composite scene images. In some embodiments, the virtual image of the end instrument may include a contour line and/or transparent entity illustrating the end instrument. As a result, the position and size of the end instrument can be shown without hindering the operator's field of view.

In some embodiments, the method 1000 may further include in the composite scene image, along an axis direction of the virtual image of the end instrument, generating a first virtual ruler for indicating a distance. The first virtual ruler may be generated along the contour of the virtual image of the end instrument, and used to show a length of the end instrument, facilitating to improve an accuracy of the operation of the operator. In some embodiments, the method of generating the first virtual ruler may be similarly implemented as the step 1703 in the method 1700.

In some embodiments, the method 1000 may further include determining a distance between the end of the main body and a surgical site, and updating, based on the distance between the end of the main body and the surgical site, the first virtual ruler to a second virtual ruler. For example, the distance between the end of the main body and the surgical site may be measured by a ranging unit on the main body, and the second virtual ruler is generated based on this distance. The second virtual ruler may include information indicated by the first virtual ruler and information about the distance between the end of the main body and the surgical site. By updating the first virtual ruler to the second virtual ruler, the length of the end instrument and the distance between the end instrument and the surgical site may be shown simultaneously, helping to further improve an accuracy of the operation of the operator. In some embodiments, the method of generating the second virtual ruler may be similarly implemented as the step 1703 in the method 1700.

In some embodiments of the present disclosure, the present disclosure further provides a computer device comprising a memory and a processor. The memory may be used to store at least one instruction. The processor is coupled to the memory, and is configured to execute the at least one instruction to perform some or all of the steps of the methods of the present disclosure, such as some or all of the steps of the methods shown in FIGS. 10-11 and FIGS. 13-17.

Figure 18:
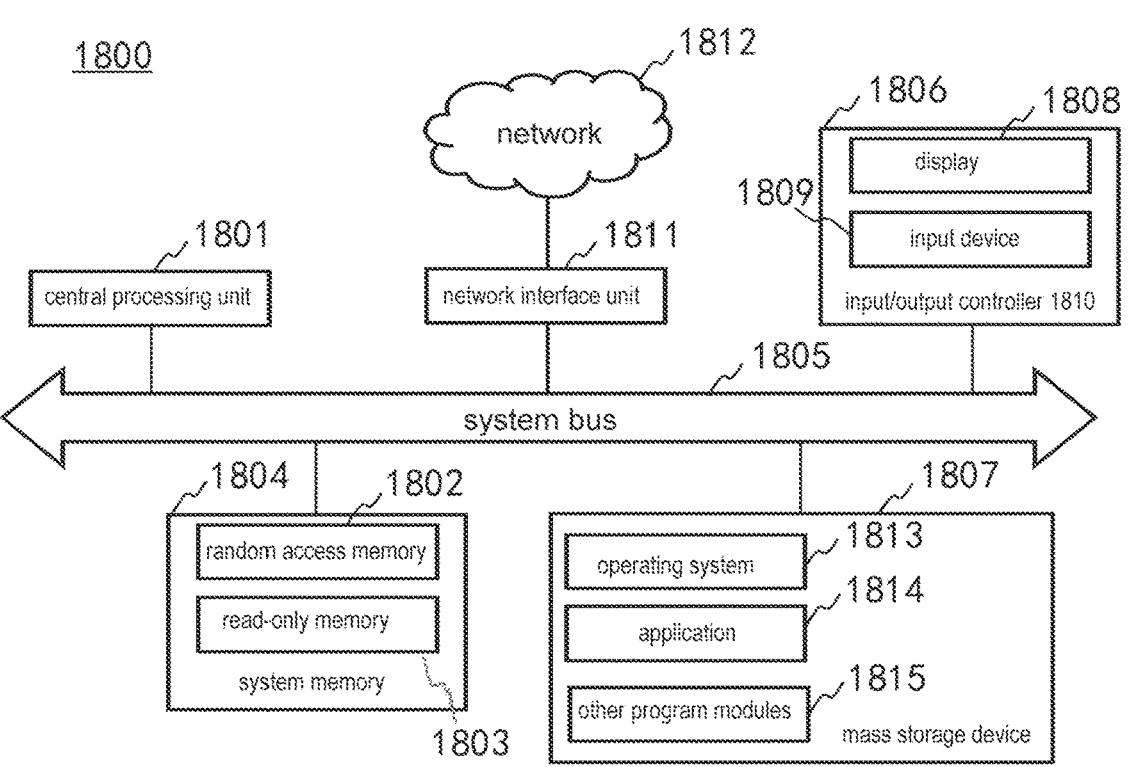
FIG. 18 shows a schematic block diagram of a computer device according to some embodiments of the present disclosure.

FIG. 18 shows a schematic block diagram of a computer device 1800 according to some embodiments of the present disclosure. Referring to FIG. 18, the computer device 1800 may include a central processing unit (CPU) 1801, a system memory 1804 including a random access memory (RAM) 1802 and a read-only memory (ROM) 1803, and a system bus 1805 connecting the various components. The computer device 1800 may further include an input/output system, and a mass storage device 1807 for storing an operating system 1813, application 1814 and other program modules 1815. The input/output device comprises an input/output control device 1810 mainly comprising a display 1808 and an input device 1809.

The mass storage device 1807 is connected to the central processing unit 1801 via a mass storage control device (not shown) connected to the system bus 1805. The mass storage device 1807 or a computer-readable medium provides non-volatile storage for the computer device. The mass storage device 1807 may include a computer-readable medium (not shown) such as a hard disk or a Compact Disc Read-Only Memory (CD-ROM) drive or the like.

Without loss of generality, the computer-readable medium may include a computer storage medium and a communication medium. The computer storage medium includes a volatile and non-volatile, removable and non-removable medium implemented by any of methods or technologies for storing information such as computer-readable instructions, data structures, program modules, or other data and the like. The computer storage medium includes RAM, ROM, a flash memory or other solid-state memory technology, CD-ROM, or other optical storage, a tape cartridge, a tape, disk storage, or other magnetic storage devices. Of course, those skilled in the art will know that the computer storage medium is not limited to the above. The above system memory and mass storage device may be collectively referred to as memory.

The computer device 1800 may be connected to a network 1812 via a network interface unit 1811 connected to the system bus 1805.

The system memory 1804 or the mass storage device 1807 is also used to store one or more instructions. The central processor 1801 implements all or part of the steps of the methods in some embodiments of the present disclosure by executing the one or more instructions.

In some embodiments of the present disclosure, the present disclosure further provides a computer-readable storage medium in which at least one instruction is stored. The at least one instruction is executed by the processor to enable the computer to perform some or all of the steps of the methods disclosed in some embodiments, such as some or all of the steps of the methods disclosed in FIGS. 10-11 and FIGS. 13-17. Examples of the computer-readable storage medium include a memory for computer programs (instructions), e.g., a read-Only Memory (ROM), a Random Access Memory (RAM), a read-only disc (Compact Disc Read-Only Memory, CD-ROM), a tape, a floppy disk, and an optical data storage device.

Figure 19:
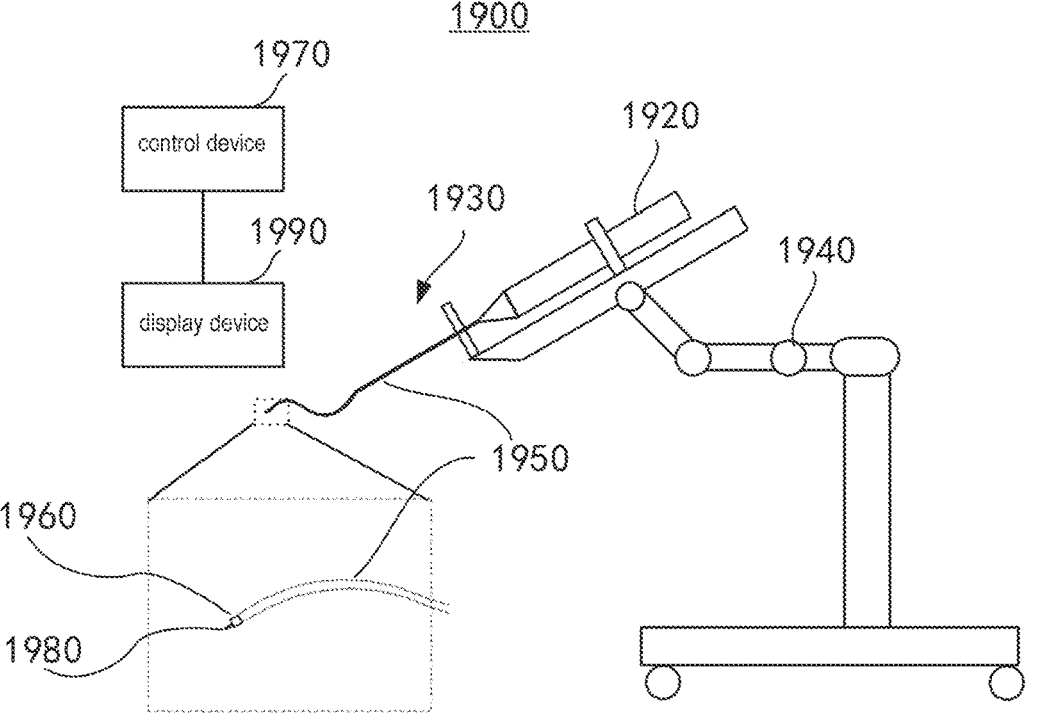
FIG. 19 shows a schematic diagram of a robot system according to some embodiments of the present disclosure.

FIG. 19 shows a schematic diagram of a robot system 1900 according to some embodiments of the present disclosure. In some embodiments of the present disclosure, see FIG. 19, the robot system 1900 may include a motion arm 1940, an endoscope 1930, a control device 1970 and a display device 1990. The endoscope 1930 includes a drive device 1920 and an operating arm 1950. The endoscope main body 1960 is disposed at a distal end of the operating arm 1950, and the endoscope 1930 includes an end instrument 1980 for performing surgical tasks. The display device 1990 is used to display a picture output by the endoscope 1930. The control device 1970 is configured to be connected with the motion arm 1940 and the drive device 1920 to control the motion of the operating arm 1950, and communicatively connected with the endoscope 1930 to process the image output by the endoscope 1930. The control device 1970 is used to perform some or all of the steps of the methods of some embodiments of the present disclosure, such as some or all of the steps of the methods disclosed in FIGS. 10-11 and FIGS. 13-17.

Note that the above are only exemplary embodiments of the present disclosure and the applied technical principles. Those skilled in the art will appreciate that the present disclosure is not limited to specific embodiments herein, and those skilled in the art can make various apparent changes, readjustments and substitutions without departing from the scope of protection of the present disclosure. Thus, although the present disclosure is described in more detail by the above embodiments, the present disclosure is not limited to the above embodiments. Without departing from the concept of the present disclosure, more other equivalent embodiments may be included, and the scope of the present disclosure is determined by the scope of the appended claims.

What is claimed is:

1. An endoscope control method, comprising:
   controlling a motion of the endoscope, the endoscope comprising a main body, a first imaging unit, a second imaging unit and an end instrument protruding from a distal end of the main body;
   obtaining a first image from the first imaging unit;
   obtaining a second image from the second imaging unit, wherein the first image and the second image have different fields of view and include images of the end instrument;
   generating, based on the first image and the second image, a composite scene image to remove an actual image of the end instrument; and
   generating a virtual image of the end instrument in the composite scene image,
   wherein the endoscope control method further comprises:
      generating, based on the first image and/or the second image, an actual scene image to display an actual image of the end instrument; and
      displaying, in response to a display mode instruction, the composite scene image with the virtual image and/or the actual scene image, wherein the display mode instruction comprises at least one of:
         a motion control instruction for controlling a motion of the endoscope;
         an end instrument operation instruction for controlling an operation of the end instrument; or
         a display mode selection instruction for selecting a display mode;
   wherein the motion control instruction comprises a first endoscope motion instruction which comprises a feed instruction or a steering instruction, and wherein the endoscope control method further comprises:

displaying, in response to the first endoscope motion instruction, the composite scene image with the virtual image; and controlling, based on the first endoscope motion instruction, the endoscope to move towards an operating area.

2. The endoscope control method according to claim 1, further comprising:

displaying, in response to the end instrument operation instruction, the actual scene image; or displaying, in response to a termination of the end instrument operation instruction, the composite scene image with the virtual image.

3. The endoscope control method according to claim 1, wherein the motion control instruction further comprises a second endoscope motion instruction;

the endoscope control method further comprises:

controlling, based on the second endoscope motion instruction, the endoscope to move away from the operating area; and displaying, in response to a distance of the endoscope away from the operating area exceeding a threshold, the composite scene image with the virtual image.

4. The endoscope control method according to claim 3, further comprising:

determining whether a distance for which the endoscope retreats exceeds a threshold; or determining whether a cumulative value of an amount of position change of a master manipulator for performing a master-slave control on endoscope that corresponds to the second endoscope motion instruction exceeds a threshold.

5. The endoscope control method according to claim 3, wherein a display mode control priority of the display mode instruction comprises at least one of:

a display mode control priority of the end instrument operation instruction being higher than a display mode control priority of the first endoscope motion instruction;

a display mode control priority of the second endoscope motion instruction being higher than a display mode control priority of the end instrument operation instruction; or a display mode control priority of the display mode selection instruction being higher than a display mode control priority of the second endoscope motion instruction.

6. The endoscope control method according to claim 1, wherein the motion control instruction further comprises an automatic exit instruction;

the endoscope control method further comprises:

controlling, based on the automatic exit instruction, the endoscope to exit from a body; and displaying, in response to the automatic exit instruction, the composite scene image with the virtual image of the end instrument.

7. The endoscope control method according to claim 1, wherein:

the display mode selection instruction comprises at least one of:

a composite scene display instruction for displaying the composite scene image with the virtual image;

an actual scene display instruction for displaying the actual scene image; or a multi-scene display instruction for displaying at least a portion of the actual scene image in a first window and displaying at least a portion of the composite scene image with the virtual image in a second window.

8. The endoscope control method according to claim 1, wherein generating the composite scene image comprises:

determining a supplementary image based on the first image or the second image, the supplementary image comprising a portion of the second image or the first image that is blocked by the end instrument;

determining a first environment image or a second environment image based on the first image or the second image, wherein the first environment image and the second environment image do not include an image of the end instrument; and stitching the first environment image or the second environment image and the supplementary image to generate a stitched image.

9. The endoscope control method according to claim 8, further comprising:

for at least one of the first image, the second image, the first environment image, the second environment image, the supplementary image or the stitched image, determining, based on the image and a previous frame image of the image, an optical flow field of the image, the optical flow field comprising optical flows of a plurality of pixels in the image;

generating a depth map of the image based on the optical flow field of the image and a pose of the imaging unit corresponding to the image, the depth map comprising depths of object points corresponding to the plurality of pixels;

determining, based on the depth map of the image and pixel coordinates of the plurality of pixels, object point spatial coordinates of object points corresponding to the plurality of pixels;

acquiring, based on the image, color information of the plurality of pixels; and performing a point cloud fusion on the image based on the color information of the plurality of pixels and the object point spatial coordinates to generate a three-dimensional point cloud.

10. The endoscope control method according to claim 9, wherein generating a depth map of the image based on the optical flow field of the image and a pose of the imaging unit corresponding to the image comprises:

determining a focus of the optical flow field based on the optical flow field of the image;

determining distances between the plurality of pixels and the focus based on the focus of the optical flow field;

determining velocities of the plurality of pixels in the optical flow field based on the optical flow field of the image;

determining a velocity of the imaging unit based on the pose of the imaging unit corresponding to the image; and determining the depth map of the image based on the distances between the plurality of pixels and the focus, the velocities of the plurality of pixels in the optical flow field and the velocity of the imaging unit.

11. The endoscope control method according to claim 1, wherein generating a virtual image of the end instrument in the composite scene image comprises:

determining a position and size of the end instrument in the composite scene image; and generating the virtual image of the end instrument in the composite scene image.

12. The endoscope control method according to claim 11, wherein the virtual image of the end instrument comprises a contour line and/or transparent entity illustrating the end instrument; and/or generating, in the composite scene image, along an axis direction of the virtual image of the end instrument, a first virtual ruler for indicating a distance.

13. The endoscope control method according to claim 12, further comprising:

determining a distance between the endoscope and a surgical site; and updating the first virtual ruler to a second virtual ruler based on the distance between the endoscope and the surgical site.

14. A robot system, comprising:

a motion arm;

an endoscope disposed at an end of the motion arm, the endoscope including:

an operating arm including at least one segment capable of being bent controllably a main body disposed at a distal end of the operating arm;

a first imaging unit for taking a first image;

a second imaging unit for taking a second image; and an end instrument configured to protrude from a distal end of the main body;

a control device configured to perform an endoscope control method; and a display device configured to display an image based on a instruction output by the control device;

wherein the endoscope control method comprises:

controlling a motion of the endoscope, the endoscope comprising a main body, a first imaging unit, a second imaging unit and an end instrument protruding from a distal end of the main body;

obtaining a first image from the first imaging unit;

obtaining a second image from the second imaging unit, wherein the first image and the second image have different fields of view and include images of the end instrument;

generating, based on the first image and the second image, a composite scene image to remove an actual image of the end instrument; and generating a virtual image of the end instrument in the composite scene image, wherein the endoscope control method further comprises:

generating, based on the first image and/or the second image, an actual scene image to display an actual image of the end instrument; and displaying, in response to a display mode instruction, the composite scene image with the virtual image and/or the actual scene image, wherein the display mode instruction comprises at least one of:

a motion control instruction for controlling a motion of the endoscope;

an end instrument operation instruction for controlling an operation of the end instrument; or a display mode selection instruction for selecting a display mode;

wherein the motion control instruction comprises a first endoscope motion instruction which comprises a feed instruction or a steering instruction, and wherein the endoscope control method further comprises:

displaying, in response to the first endoscope motion instruction, the composite scene image with the virtual image; and controlling, based on the first endoscope motion instruction, the endoscope to move towards an operating area.

15. The robot system according to claim 14, wherein, an optical axis of the first imaging unit and an optical axis of the second imaging unit are parallel to an axis of the main body, respectively; and an axis of the end instrument is parallel to the axis of the main body and deviates from a connecting line between the first imaging unit and the second imaging unit.

16. The robot system according to claim 14, wherein, the end instrument includes at least one first electrode, at least one second electrode and an insulating body, wherein the at least one first electrode and the at least one second electrode are alternately arranged on a circumferential outward side of the insulating body, at least a portion of the first electrode is exposed, and at least a portion of the second electrode is exposed, and/or the main body of the endoscope comprises an inner annular member and an outer annular member, the end instrument comprises a first electrode and a second electrode, the first electrode is mounted onto the inner annular member, the second electrode is mounted onto the outer annular member and surrounds at least a portion of the first electrode at an interval in a radial direction; and/or the operating arm comprises at least one structural bone, a fixation disc and at least one spacer disc, the at least one structural bone passes through the at least one spacer disc and its end is fixedly connected to the fixation disc.

17. A non-transitory computer-readable storage medium for storing at least one instruction, that when executed by a computer, causes the computer to perform an endoscope control method, wherein the endoscope control method comprises:

controlling a motion of the endoscope, the endoscope comprising a main body, a first imaging unit, a second imaging unit and an end instrument protruding from a distal end of the main body;

obtaining a first image from the first imaging unit;

obtaining a second image from the second imaging unit, wherein the first image and the second image have different fields of view and include images of the end instrument;

generating, based on the first image and the second image, a composite scene image to remove an actual image of the end instrument; and generating a virtual image of the end instrument in the composite scene image, wherein the endoscope control method further comprises:

generating, based on the first image and/or the second image, an actual scene image to display an actual image of the end instrument; and displaying, in response to a display mode instruction, the composite scene image with the virtual image and/or the actual scene image, wherein the display mode instruction comprises at least one of:

a motion control instruction for controlling a motion of the endoscope;

an end instrument operation instruction for controlling an operation of the end instrument; or a display mode selection instruction for selecting a display mode, wherein the motion control instruction comprises a first endoscope motion instruction which comprises a feed instruction or a steering instruction, and wherein the endoscope control method further comprises:

displaying, in response to the first endoscope motion instruction, the composite scene image with the virtual image; and controlling, based on the first endoscope motion instruction, the endoscope to move towards an operating area.

* * * * *